(12) United States Patent
Crandall et al.

(10) Patent No.: US 11,154,244 B2
(45) Date of Patent: Oct. 26, 2021

(54) AUTOMATED TURF TESTING APPARATUS AND SYSTEM FOR USING SAME

(71) Applicant: Biocore LLC, Charlottesville, VA (US)

(72) Inventors: Jeff Crandall, Charlottesville, VA (US); Richard Kent, Keswick, VA (US); Edward Meade Spratley, Charlottesville, VA (US); Jared Yoder, Aroda, VA (US); Thomas Cisneros, Petaluma, CA (US); Philipe Aldahir, Chattanooga, TN (US); Jeff Lipari, Petaluma, CA (US)

(73) Assignee: BioCore LLC, Charlottesville, VA (US)

( * ) Notice: Subject to any disclaimer, the term of this patent is extended or adjusted under 35 U.S.C. 154(b) by 0 days.

(21) Appl. No.: 17/192,752

(22) Filed: Mar. 4, 2021

(65) Prior Publication Data
US 2021/0275099 A1    Sep. 9, 2021

Related U.S. Application Data

(60) Provisional application No. 62/985,126, filed on Mar. 4, 2020.

(51) Int. Cl.
| | |
|---|---|
| *A61B 5/00* | (2006.01) |
| *A61B 5/103* | (2006.01) |
| *G01N 3/00* | (2006.01) |
| *G01N 3/08* | (2006.01) |
| *G01N 3/32* | (2006.01) |

(Continued)

(52) U.S. Cl.
CPC .......... *A61B 5/6807* (2013.01); *A61B 5/1038* (2013.01); *G01N 3/00* (2013.01);
(Continued)

(58) Field of Classification Search
CPC ................... G01N 19/02; G01N 19/10; G01N 2203/0025; G01N 2203/0246;
(Continued)

(56) References Cited

U.S. PATENT DOCUMENTS

| | | | |
|---|---|---|---|
| 2,638,776 A | * | 5/1953 | Aines ....................... G01N 3/56 73/7 |
| 5,259,236 A | | 11/1993 | English |

(Continued)

FOREIGN PATENT DOCUMENTS

| | | | |
|---|---|---|---|
| CN | 108489653 A | * | 9/2018 |
| CN | 108903137 A | * | 11/2018 |

(Continued)

OTHER PUBLICATIONS

Application No. PCT/US2021/020917, International Search Report and Written Opinion dated Jun. 7, 2021.

*Primary Examiner* — Jonathan M Dunlap
(74) *Attorney, Agent, or Firm* — Woods Rogers PLC; Nathan A. Evans

(57) ABSTRACT

A mobile apparatus that is automated to measure controlled and applied forces to sport surfaces allowing for safety assessment of athletic apparel and athletic surfaces, such as natural or artificial turf. The apparatus is capable of using not only horizontal and vertical forces, but also rotational moments, and all prescribed forces and moments in combination at the same or different times. The apparatus and related system can apply horizontal and vertical forces, and rotational moments, and link these forces and moments together and combine them to more closely mimic behavior of human foot during an athletic movement, thereby applying and measuring interactions between all forces and moments at the same or different times.

28 Claims, 23 Drawing Sheets

(51) Int. Cl.
*G01N 19/10* (2006.01)
*G01N 3/42* (2006.01)
*G01N 3/56* (2006.01)
*G01N 19/02* (2006.01)
*G01N 3/40* (2006.01)
*A43B 5/00* (2006.01)
*G01N 33/24* (2006.01)
*G01L 5/00* (2006.01)
*G01N 33/00* (2006.01)

(52) U.S. Cl.
CPC ............... *G01N 3/08* (2013.01); *G01N 3/32* (2013.01); *A43B 5/00* (2013.01); *G01L 5/00* (2013.01); *G01N 3/40* (2013.01); *G01N 3/42* (2013.01); *G01N 3/56* (2013.01); *G01N 19/02* (2013.01); *G01N 19/10* (2013.01); *G01N 33/24* (2013.01); *G01N 2033/008* (2013.01); *G01N 2203/0025* (2013.01); *G01N 2203/0246* (2013.01)

(58) Field of Classification Search
CPC ............ G01N 33/24; G01N 3/42; G01N 3/40; G01N 3/56; G01N 3/08; G01N 3/00; G01N 3/32; G01N 2033/008; A43B 5/00; G01L 5/00; A61B 5/6807; A61B 5/1038
See application file for complete search history.

(56) References Cited

U.S. PATENT DOCUMENTS

| | | | | |
|---|---|---|---|---|
| 6,854,316 B2* | 2/2005 | Hage | ................. | G01N 19/02 73/9 |
| 7,290,436 B2* | 11/2007 | Olde Weghuis | ........ | G01N 19/02 73/10 |
| 7,628,059 B1* | 12/2009 | Scherbring | ............. | E02D 1/022 73/84 |
| 8,327,693 B2* | 12/2012 | Scherbring | ............. | G01N 3/40 73/84 |
| 9,464,980 B2* | 10/2016 | Yngve | .................. | G01N 19/02 |
| 10,976,237 B2* | 4/2021 | Gray | ..................... | G01N 19/02 |
| 10,983,037 B2* | 4/2021 | Sick | ...................... | G01N 19/02 |
| 2004/0149005 A1* | 8/2004 | Hage | .................... | G01N 19/02 73/9 |
| 2005/0178184 A1* | 8/2005 | Stroppiana | ............... | G01N 3/48 73/12.13 |
| 2006/0130556 A1* | 6/2006 | Olde Weghuis | ....... | G01N 19/02 73/9 |
| 2011/0203356 A1* | 8/2011 | Scherbring | ............. | G01N 3/40 73/84 |
| 2012/0297889 A1* | 11/2012 | Yngve | ................... | G01N 19/02 73/818 |
| 2019/0302003 A1* | 10/2019 | Sick | ....................... | G01N 19/02 |
| 2019/0346261 A1* | 11/2019 | Carson | ................. | G01N 33/24 |
| 2019/0369005 A1* | 12/2019 | Gray | ..................... | G01N 19/02 |

FOREIGN PATENT DOCUMENTS

| | | | | |
|---|---|---|---|---|
| JP | 5883657 B2 | 3/2016 | | |
| WO | WO-02063279 A1 * | 8/2002 | ............. | G01N 19/02 |
| WO | 2005024396 A1 | 3/2005 | | |
| WO | WO-2005024396 A1 * | 3/2005 | ............. | G01N 19/02 |
| WO | WO-2018132650 A1 * | 7/2018 | ............... | G01B 5/20 |
| WO | 2019213708 A1 | 11/2019 | | |

* cited by examiner

FIGURE 10 - Actuators

FIGURE 15 – Shaft Actuation Assembly

FIGURE 16 – Shaft Actuation Assembly – Cross-section

FIGURE 17 - Shaft Bearing Assembly – SIDE

Footform – ISO

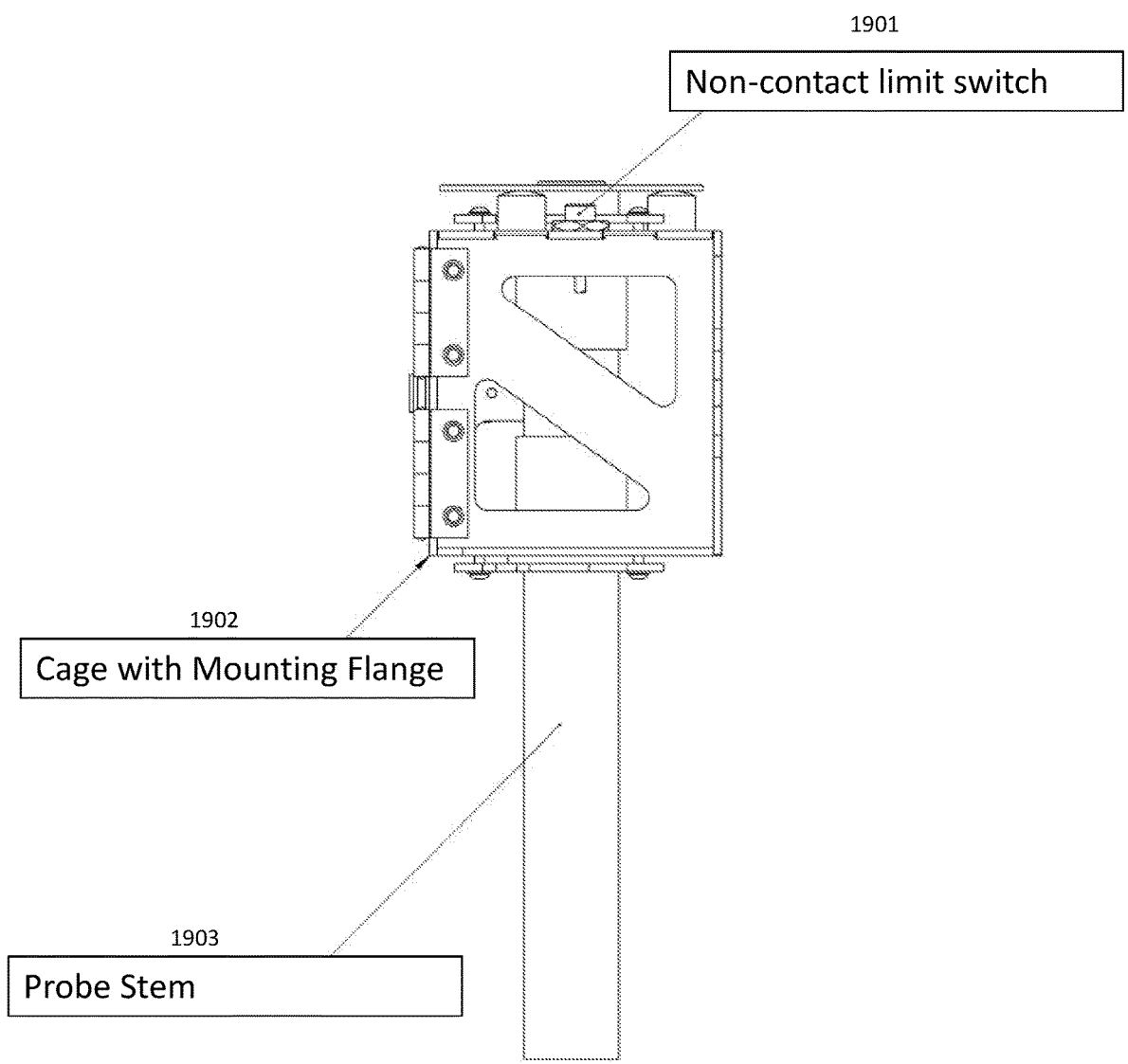
FIGURE 19 - Turf Datum Finder – SIDE

Impact Tester & Consolidated Data Capture – Automated by Solenoid

Actuation Architecture

Controller States
- 11 Controller States
- Lights
  - Red blocks = flashing red
  - Green blocks = solid green
  - E-stop = flashing red and green
- Work to complete
  - Add cable preload states FIGURE 22 - Device Control Diagram
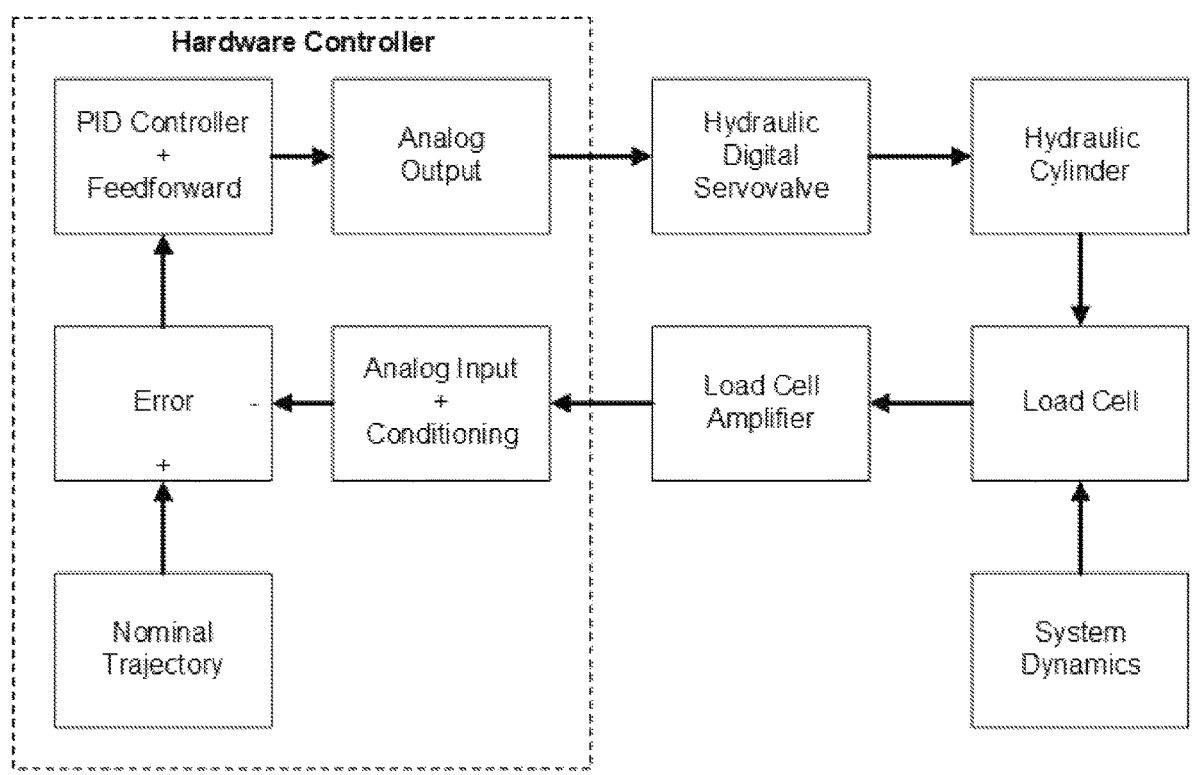

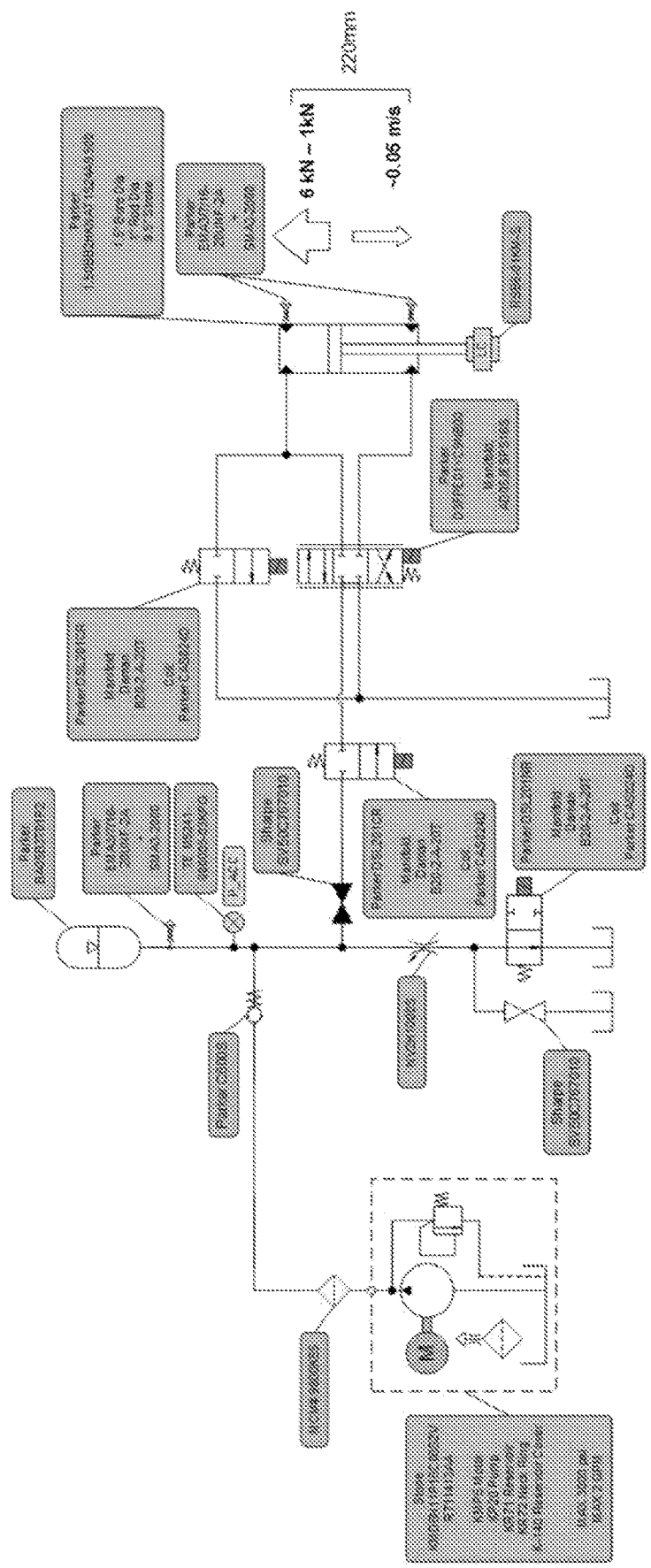
FIGURE 23 - Device Power Architecture

AUTOMATED TURF TESTING APPARATUS AND SYSTEM FOR USING SAME

CROSS-REFERENCE TO RELATED APPLICATIONS

The present application relies on the disclosures of and claims priority to and the benefit of the filing date of U.S. Provisional Application No. 62/985,126, filed Mar. 4, 2020. The disclosures of that application are hereby incorporated by reference herein in their entireties. Information from the following related website is also hereby incorporated by reference in its entirety:
https://www.figma.com/proto/
PeRRW6ZRPMwgMkVAZ4n6yl/BEAST-UI?node-id=4%3A11&viewport=9974%2C-566%2C0.7194263339042664&scaling=min-zoom

BACKGROUND OF THE INVENTION

Field of the Invention

The present invention relates to a mobile apparatus and associated system that is completely or partially automated and is configured to measure sport surface (e.g., sport turf) characteristics and the safety of athletic apparel accurately and consistently in an apparel-to-surface interaction, in a manner that is quantifiable and repeatable. This application uses sport turf as an example but is not limited to sport turf, because the invention can be used with non-grass and non-turf surfaces using an appropriate foot form, instrumentation, and/or loads and motions particular to a certain sport (e.g., tennis, baseball, football, soccer, and so on). In examples only, sport turf is considered to be a naturally or artificially grassed surface and the immediate underlying environment, managed and prepared for fast and aggressive playing such as in American Football and Soccer. With reliable gameday, practice, or other data, causes and dangers of injury on natural or synthetic turf, using particular athletic apparel that interact with the turf can be better understood, predicted, and reduced through better field and apparel characterization and rating(s). Moreover, as described herein, the shoe/surface interaction contributes to athletic performance, which, according to the present invention, could also be better characterized, understood, predicted, and even enhanced.

Accurately and consistently quantifying turf conditions, as well as the effect of turf conditions on athletic apparel in situations and conditions that mimic athletic movement, can be used to reduce athletic injury occurrences, improve player performance, establish accurate, independent standards for artificial turf manufacturing, installation, and maintenance, prevent expensive stadium rework, and can lead to standardizing field and turf assessments across sports fields, including but not limited to American football and soccer, just to name a couple examples. With the instrumentation, system, products and methods described herein, and a sport-specific foot form, these tests could be performed on clay surfaces (e.g., baseball skins, warning track, tennis courts), hard surfaces (e.g., tennis, pickleball, volleyball, basketball), sand surfaces (e.g., beach volleyball, bocce, horse tracks), and other grassed (artificial or natural) surfaces such as horse tracks and cricket fields/pitches. With the present invention's instrumentation, the apparatus and system could also be used to quantify performance of a golf club or surface by characterizing a club to ground interaction, including an interaction that results in a portion of the playing surface being removed by the club head. Such testing may also be used in non-athletic environments where synthetic or natural surfaces are utilized. In order to accomplish adequate testing for quantifying turf conditions and effects of athletic apparel, the apparatus taught herein uses not only horizontal and vertical forces, but also torsional forces, and all three forces in combination at the same or different times. Thus, the apparatus and system can apply horizontal, vertical, and torsional forces, and link these forces together and combine them into a single motion to more closely mimic behavior of, for example, a human foot, leg, or entire body during an athletic movement, thereby applying and measuring interactions between all three forces at the same or different times.

Description of Related Art

In the National Football League ("NFL"), for example only, there is a significantly higher rate of non-contact injuries to lower limbs on synthetic turf than on natural turf (i.e., 28-69% higher). There have been ongoing attempts to determine why this is, however, the results are inconclusive. This suggests that the data currently being collected can be improved upon. Currently, typically before every game, the turf is manually inspected, and the data is recorded for reference if an injury were to occur.

While current on-field tests include impact hardness, infill depth and evenness, soil moisture content, surface shear resistance using a shear vane, percentage ground cover, visual inspection, and stability rating (post-game), the current tests have proven to be inconsistent, non-comprehensive, and subjective. Injuries continue to be a problem in all sports despite currently available safeguards, and a need exists for an improved way to attempt to decrease athletic injuries across all sports, especially those played on turf.

SUMMARY OF INVENTION

Due to the current limitations, it is an object of the current invention to allow for data collection on, for example, shoe-to-turf interaction while subject to applied forces in order to properly correlate injury to turf characteristics, and/or characteristics of the cleat or shoe. In aspects, data collection might include, for example, kinetic and kinematic data during the shoe-turf interaction, measurement of turf characteristics through additional measuring devices, and recording of characteristics of the shoe and/or turf used for the shoe-turf interaction test. Because of the capabilities of the current invention, when injuries occur, the incidence of injury can be traced back to the turf data or apparel data collected by the inventive apparatus and compared amongst other cases of injury or, alternatively, with cases of non-injury. Once common injury metrics or injury risks are established, by way of example only, mechanical parameters measured can be minimized in the manufacture of turf or athletic apparel, thereby reducing injuries based on quantifiable data. To accomplish this, the current invention is, in aspects, mobile and completely- or partially-automated, and configured to provide reliable data that is repeatable and reproducible.

It is an object of the current invention to test the safety of artificial or natural turf and/or athletic apparel, especially shoes including but not limited to cleats, using a shoe-surface tester that determines and analyzes the mechanical interactions between shoes and an athletic playing surface/turf and performs other measurements commonly taken on turf, and/or determines and analyzes whether the shoes and/or playing surface are up to standards and/or deemed safe for athletic events. The device simulates and measures shoe-to-turf interactions at loads and rates created or generated by athletes during performance up to and including those deemed to be injurious. This involves measuring displacement, velocity, and acceleration components of the shoe and/or foot form in all directions, as well as in rotation, and any combination of these forces at the same or different times. The apparatus may apply or measure all components (dx, dy, dz, rx, ry, rz) of six degrees of freedom forces and moments of the shoe and or foot form.

The apparatus may use a foot form connected to a system of nested frames or a Stewart platform to accomplish this. Thus, the cleat is actuated through its prescribed load or positional path by a mechanism capable of imparting and withstanding the significant forces and moments without unwanted mechanical deformation, friction, or fatigue that might otherwise influence the data collected. In embodiments, the device may also automate or assist with:

a) Computer-aided visual inspection of the surface during the shoe-surface interaction using high-speed (e.g., by way of example only, around 500 fps) camera(s) aided through machine learning visual recognition technologies with data synchronization, as well as photographic inspection of the surface before and/or after the test to identify foreign objects, quality of the artificial or natural turf, measure ground cover of natural turf, or perform other analyses such as surface evenness or grass coverage/density.

b) Measurement of Energy absorption and rebound/return through measurement of acceleration of a mass or mass-spring system dropped onto turf, through an on-board data collection system, and reporting of this data to the user.

c) Measurement of surface hardness (e.g., Head Injury Criterion measure; Gmax acceleration metric), using devices specified in ASTM F1702 and/or ASTM F355 or other drop test standards, collected through an on-board data collection system, and reporting of this data to the user.

d) Depth measurement (e.g., infill depth and/or evenness);

e) Assessment of Surface stability using, for example, surface shear resistance through the use of a connected shear vane;

f) Detection of Turf moisture levels;

g) Measurement of environmental factors, such as air temperature, ground temperature, air humidity, or other factors;

h) Characterization of Field maintenance; and/or i) Measurement of the top surface of the turf, relative to a datum on the invention, and reporting of that info back to the data collection system.

It is a further object of the current invention to fully characterize turf in a way sufficient to direct changes to the turf and/or shoes for improved performance and/or injury prevention. This mechanism will incorporate all or part of the tests in a controlled manner. By actuating test modes, the system can rely on the data being consistent across stadiums as human-to-human variability inherent in testing with manually powered devices is removed from the process. For example, the system may automatically restrict or fix degrees-of-freedom as appropriate for the desired test mode. The system may also automatically raise or lower the footform for the test, as appropriate. The system may also incorporate locational measurements of the top surface of the test surface into test actuation or data processing. To maintain safety, the system may display the current "state" of the system (for example, whether the system is safe for manual operations or ready to complete a test). Existing tests that will be automated are, by way of example only, surface hardness and/or energy absorption and/or return, infill depth and evenness, soil moisture content, surface shear resistance, and/or percentage ground cover detection. In addition to actuating existing tests, this improved system will also have temperature, pressure, and humidity sensors. Finally, the device will utilize a translation-rotation foot-form that can be shod with various footwear that in turn can engage with the ground to analyze shoe or cleat release dynamics.

The foot-form is representative of an athlete's foot in a cleat or shoe and is interchangeable for customizability. This extremity may have roll, pitch, and yaw adjustability to collect data on varying cleat-to-turf interface angles, as well as allow adjustment in the angle of the "toe" of the footform relative to the rest of the footform to approximate flexion of the foot about the MTP joint, yet hold these adjustments fixed in a static pose while testing is occurring. This end effector will be attached to its translation and rotation actuation mechanism via a multi-axis load cell, in aspects. This load cell will collect force and moment data on the foot-form as it moves relative to the turf via, for example, a data acquisition unit. The data collector, such as a computer, will also be recording data from rotational and translational displacement sensors to detect linear position and velocity of the shoe as well as angular rotations and velocities of the shoe. Accelerations of the foot-form may also be measured to either characterize the interaction of the shoe with the turf or, alternatively, to allow characterization of the inertial effects of the device during testing.

In other embodiments, the invention described herein is an apparatus configured to apply controlled horizontal and vertical forces and rotational moments to an end effector (footform) as prescribed, wherein the applied forces and moments mimic a behavior of a human foot or other body part during an athletic movement or reflect forces and/or moments associated with injury and/or performance of a subject's foot or other body part (e.g., the loads generated by football players in the NFL), wherein applying and measuring interactions between prescribed forces, rotational moments, and rotational and linear displacements allows for a safety and/or performance evaluation of a subject, athletic apparel, or an athletic playing surface.

In another embodiment, the invention described herein is an apparatus configured to apply controlled horizontal, vertical, and/or rotational displacements to an end effector (footform) as prescribed, wherein the applied displacements mimic a behavior of a human foot or other body part during an athletic movement or reflect displacements associated with injury and/or performance of a subject's foot or other body part (e.g., motion profiles resulting from athletic tasks resulting in foot/surface interaction during football playing), wherein applying and measuring interactions between prescribed forces, rotational moments, and rotational and linear displacements allows for a safety and/or performance evaluation of a subject, athletic apparel, or an athletic playing surface.

BRIEF DESCRIPTION OF THE DRAWINGS

The accompanying drawings illustrate certain aspects of embodiments of the present invention and should not be used to limit the invention. Together with the written description the drawings explain certain principles of the invention.

FIG. 19 is a depiction of the apparatus for athletic apparel and turf testing, including labeled aspects comprising parts of the apparatus, according to one embodiment of the present invention.

FIG. 22 is a flowchart of the device control according to one embodiment of the present invention.

FIG. 23 is a diagram of the device power architecture according to one embodiment of the present invention.

DETAILED DESCRIPTION OF INVENTION

Figure 1:
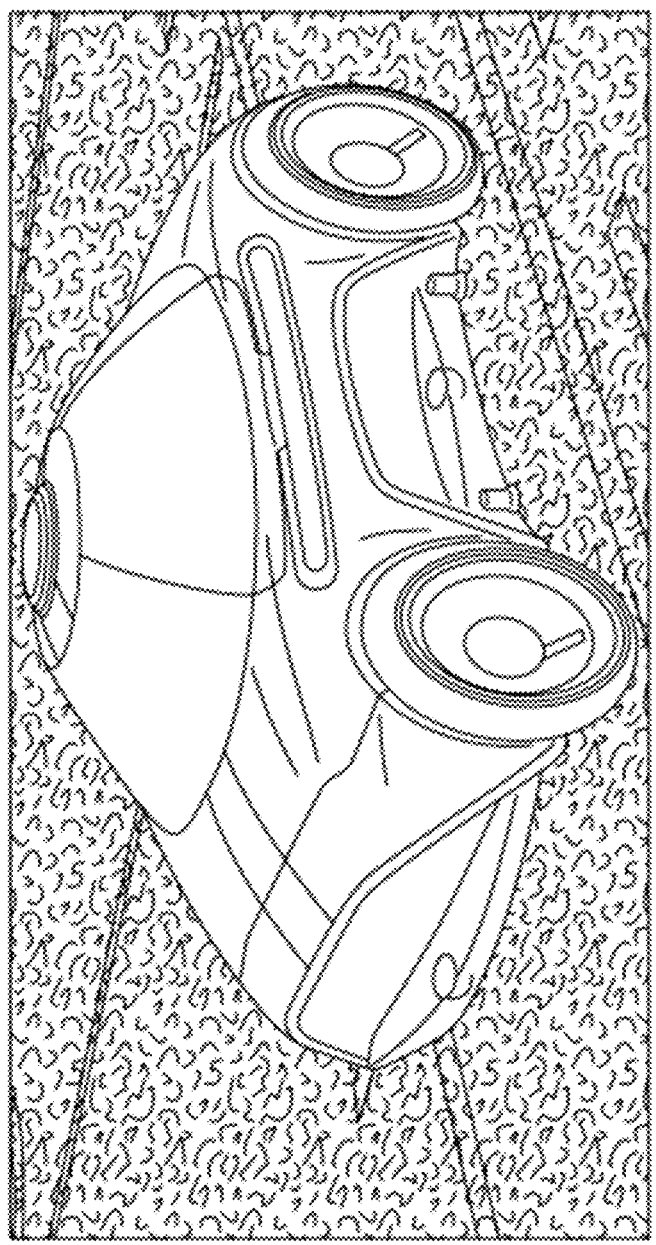
FIG. 1 is a depiction of the apparatus for athletic apparel and turf testing, according to one embodiment of the present invention.

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

The present invention can be described in terms of, for example, a foot-form assembly that is preloaded into the ground or turf sample via a tunable vertical load actuator. The apparatus and associated system can impose a constant and/or dynamic or variable horizontal force (and/or rotational torque) on the foot-form assembly while collecting motion profile data on the cleat/shoe as it engages and releases from the turf. In addition to measurement of the displacements associated with applied forces, the system is also capable of logging the minimum required force required to achieve such release from the turf fibers, infill, and overall construction. The minimum force required for cleat/shoe motion relative to the turf matters because this value potentially represents the forces that a player's leg or other body part will experience when loaded in a similar manner to an athlete representative system. This data, along with existing tests results (which will be automated, in aspects), will all be recorded and saved, in aspects. This data can be used to identify the differences in quality of synthetic turf, and the quality of athletic apparel, during injury (or non-injury) compared to the characteristics of natural turf, synthetic turf, non-injury situations, and/or safer or less safe athletic apparel. In addition to data collected during the shoe-turf interaction test, characteristics of the shoe or turf used for the test can be saved and linked with the test data.

The current invention allows for closed-loop control, wherein the system is capable of monitoring force or torque being applied and controlling the force or torque in order to, in aspects, maintain a constantly applied force or torque in a controlled and constant manner. However, in aspects, the apparatus does not necessarily need to provide force or torque in a constant manner and situations may arise where force or torque will not be applied in such a manner; rather the applied force or torque will be variable and/or adjustable. In aspects, the system measures impedance, such that it applies displacement or velocities and measures forces/torques, for example. The system may also apply and measure admittance, therein applying a force/torque and measuring displacement or velocity; thus, the system may be configured to apply a particular force/torque in order to measure the impact on, for example, an athletic shoe, a human body or body part, and/or real or synthetic turf.

In some instances, the system will use prior data knowing what forces or torques typically, usually, or sometimes cause injury in order to maintain input force/torque applied by the apparatus to determine displacement or movement of a shoe, in aspects, for a given shoe-to-turf combination(s). In embodiments, this may result in a rating or ranking of a shoe and/or turf; in aspects, it can be a pass/fail test, meaning a determination is made whether an athlete can use a particular shoe or not (is it safe, or less safe, or is it unsafe?). Also, based on test results with a given cleat, shoe or generic representation of a shoe-turf interface, the system can verify condition and maintenance of a field, e.g., within tolerances.

In aspects, the current invention tests mechanical interactions between the cleat- or shoe-to-turf interface using a translation test and a rotation test, and force and motion data are recorded via data acquisition, and therefore the system is capable of recording accurate and repeatable results. In aspects, the apparatus is configured to collect on-field displacement, velocity, force and torque data, record impact hardness, measure infill (turf), analyze surface stability (grass), read surface moisture content, perform visual inspection (e.g., via camera or drone), and/or upload or download data manually or automatically.

In aspects, the apparatus processes and displays data tailored for a certain target audience. In aspects, there might be some "hard-coded" data with some data analysis built in locally, remotely, or on a server. In another example, the analysis may be performed online via analysis of metadata stored in a server.

The system is capable of objectively scoring surfaces and footwear, and evaluating geographical compliance of a surface with a standard or protocol (using, for example, GPS to evaluate an entire field area or a portion of a field area and recommending localized intervention/maintenance).

Figure 3:
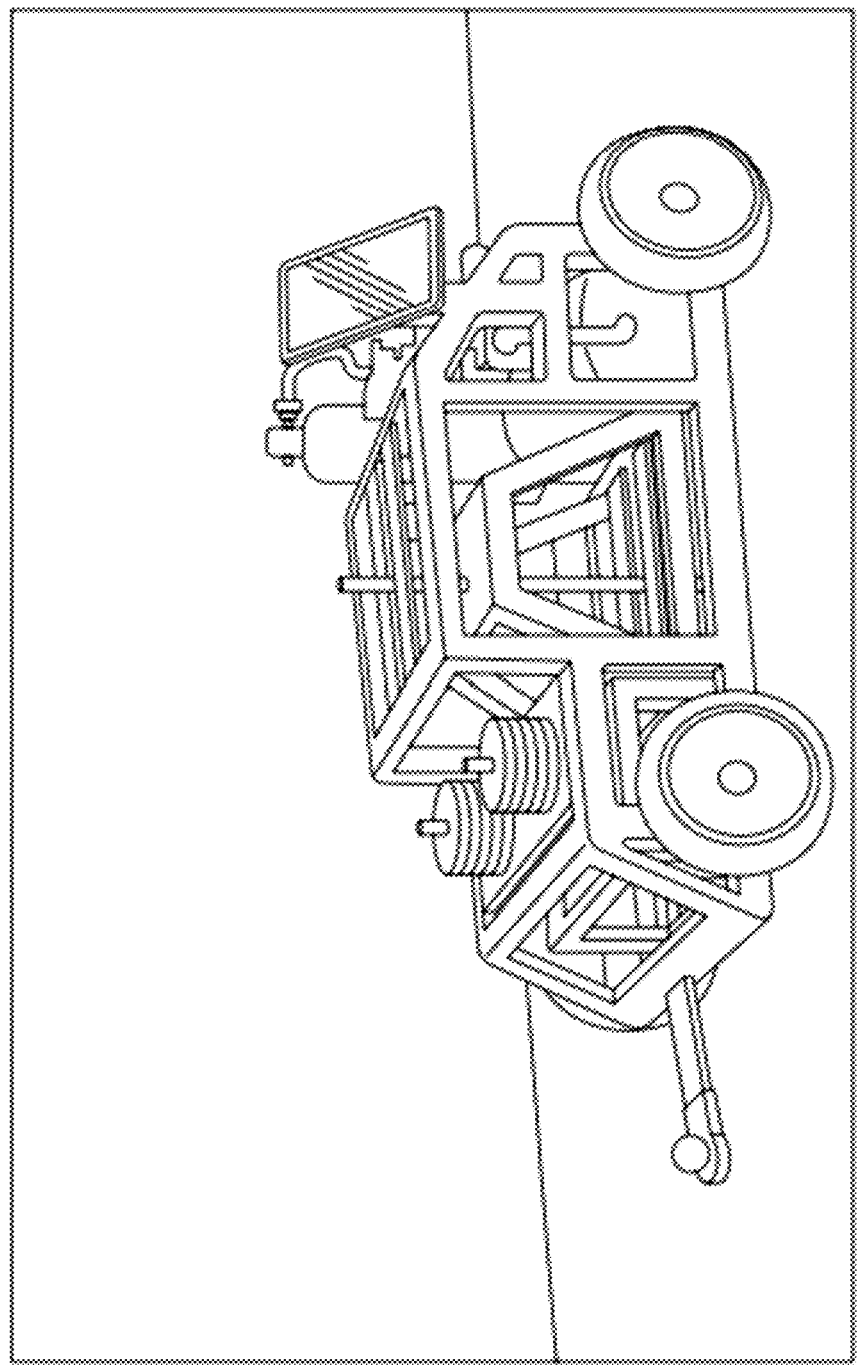
FIG. 3 is a depiction of the apparatus for athletic apparel and turf testing, according to one embodiment of the present invention.
Figure 4:
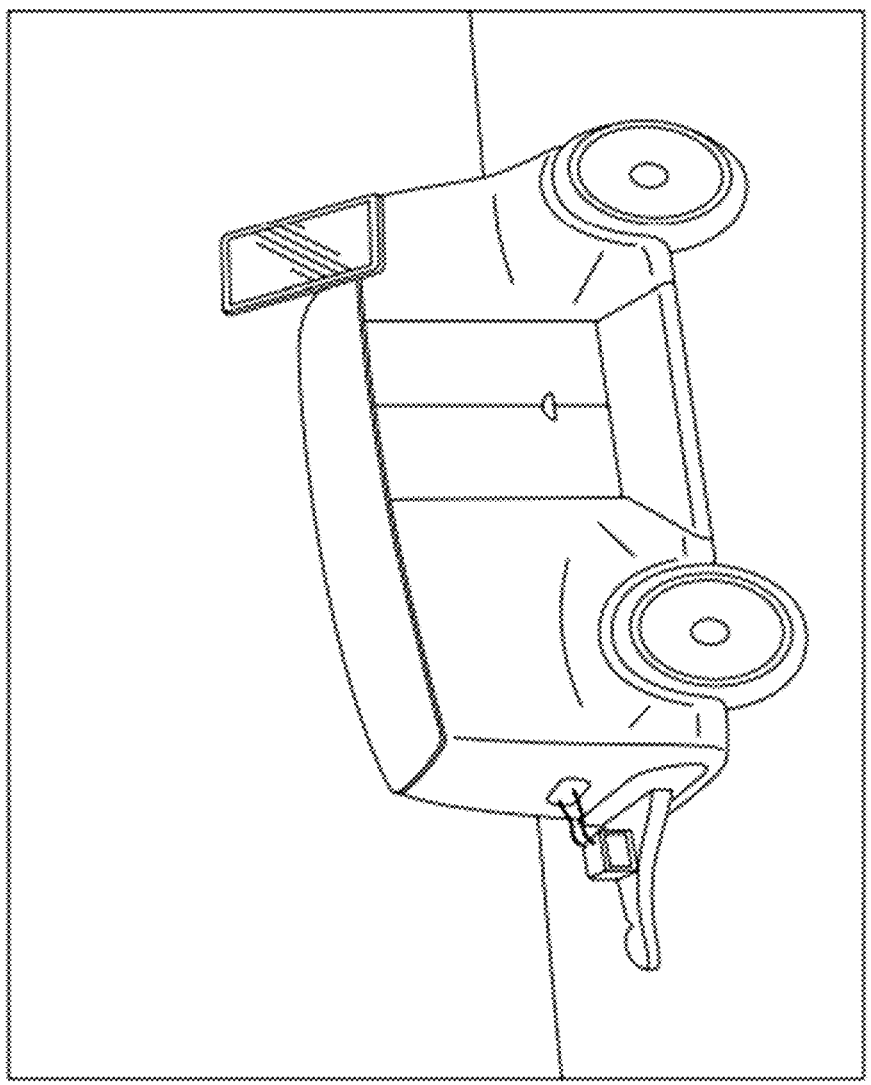
FIG. 4 is a depiction of the apparatus for athletic apparel and turf testing, according to one embodiment of the present invention.
Figure 5:
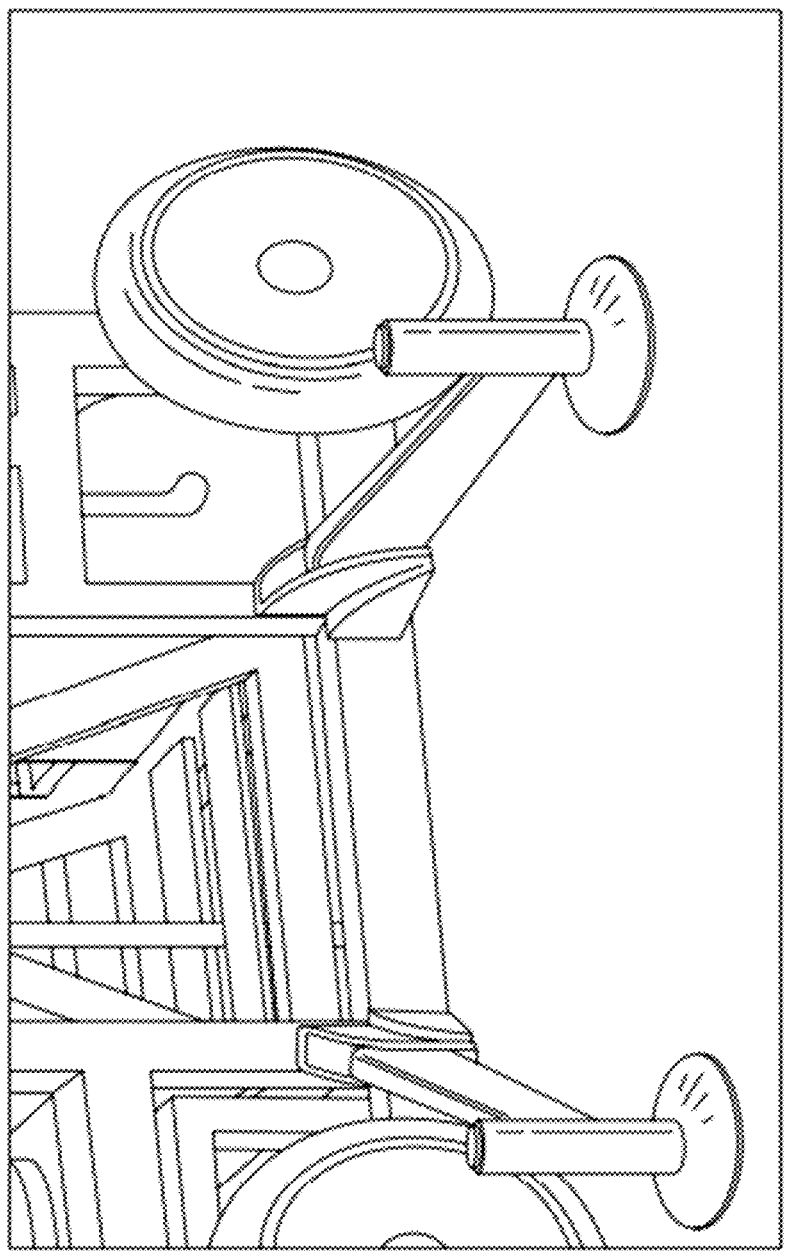
FIG. 5 is a depiction of the apparatus for athletic apparel and turf testing, according to one embodiment of the present invention, including stability fly outs for anchoring the device during testing and/or use.

Turning to the figures, in FIGS. 1-6, and FIGS. 7-9 embodiments are shown comprising certain aspects of the apparatus. In aspects, the apparatus is mobile, wherein the unit may be driven, may be autonomously driven, or may be attached to another vehicle, such as a truck, car, or golf cart (see, e.g., tow hitch attachment or trailer hitch 701, 801, 901). The apparatus may also comprise deployable outriggers, fly outs, or other mechanisms to secure or stabilize the apparatus (711, 811), such as on the turf surface to be tested. (See also, FIG. 5, showing one possible way to secure or stabilize the apparatus during testing.) In aspects, the wheels of the apparatus may be passive, if for example it is towed, but in other embodiments the apparatus may be self-powered in order to be driven by a user or driven autonomously, or by remote control. In embodiments, the apparatus will comprise a data port (706, 806), computer processor, antenna, memory storage unit, receiver, transmitter, controller, battery, charger, charging port, and other electrical components. In aspects, the apparatus may include global positioning systems (GPS) or other devices to, for example, register its position relative to the field or surface being tested. The apparatus may comprise a data acquisition system (DAQ) (709, 809), camera 821, actuator drivers (708, 808), and/or control unit (710, 810). In preferred embodiments, the apparatus will not only test cleat/shoe and surface interaction, but also include sensors to test the field conditions, such as a surface impact hardness sensor 716 and a soil moisture sensor 715, and/or an infill depth probe (712, 812). (See FIGS. 7-9.) Regarding the shoe-surface testing aspects, the apparatus may also comprise a test cleat displacement sensor 823, cleat actuator 822, vertical preload actuator (703, 803), transmission (704, 804), adjustment mechanism (705, 805), a test cleat wrench sensor (713, 813) (such as a multi-axis load cell or multiple single axis load cells), an attachment mechanism (such as a plate), and a test cleat (714, 814) for example on a foot form. In aspects, some of the described elements or all of the described elements may be attached directly or indirectly to the apparatus chassis (702, 802, 707). The apparatus may also comprise an Emergency Power Off (EPO). In aspects, see FIG. 8, the apparatus may include basic cosmetics 817, weatherizing components 818, an operator user interface 819, and process automation 820.

In FIGS. 1 and 4, an embodiment of the apparatus is shown also comprising basic cosmetic components (such as, e.g., material covering the internal mechanisms of the apparatus, like panels or molded plastic), weathering protective elements, an operator user interface, and limited process automation. In other embodiments, the apparatus will comprise a camera or other mechanisms to visually inspect the surface, including turf surface. The apparatus may include the camera attached to the apparatus or employ a drone to hover above the surface for visual inspection.

Figure 7:
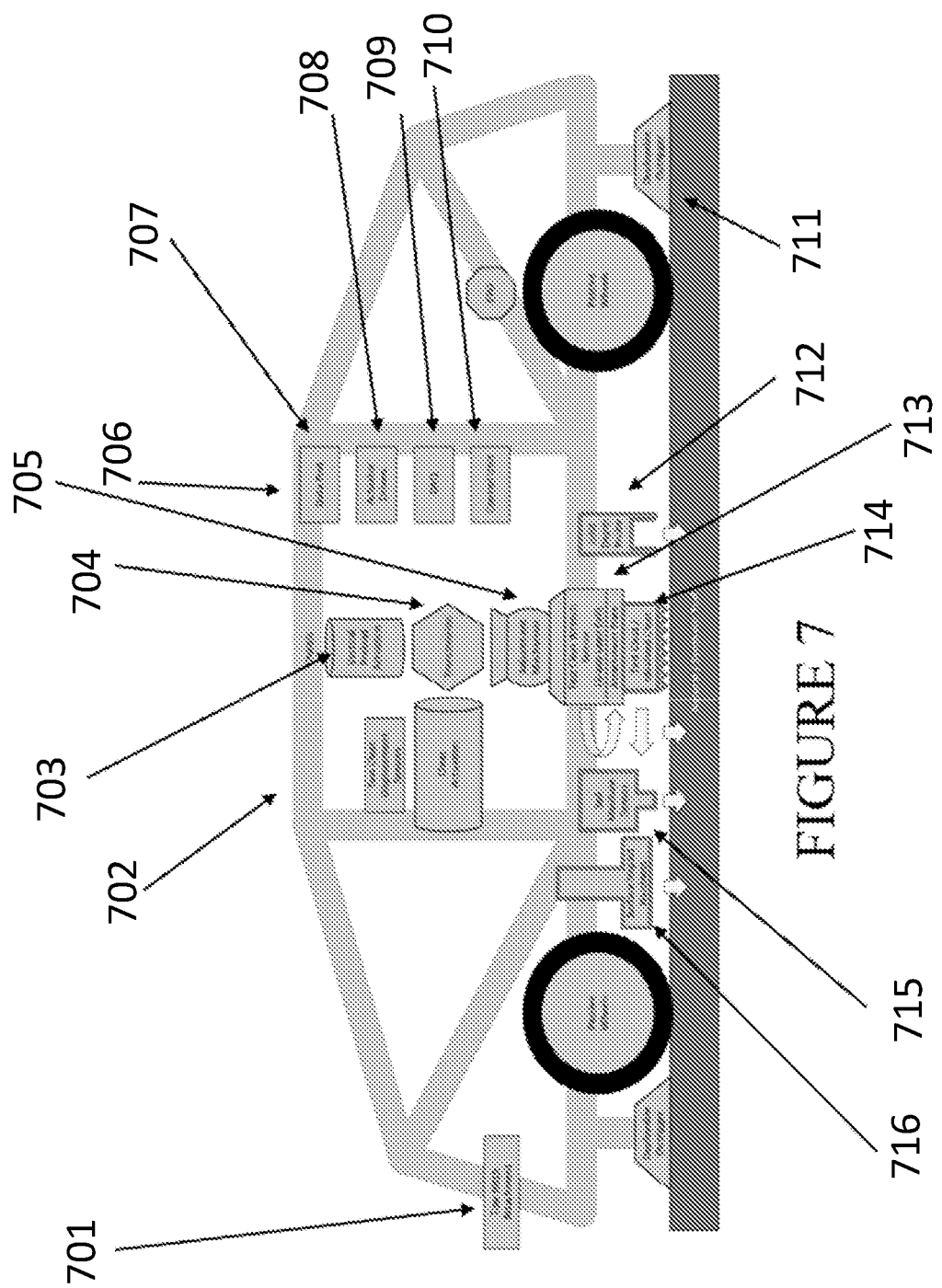
FIG. 7 is a depiction of the apparatus for athletic apparel and turf testing, including labeled aspects comprising parts of the apparatus, according to one embodiment of the present invention.
Figure 8:
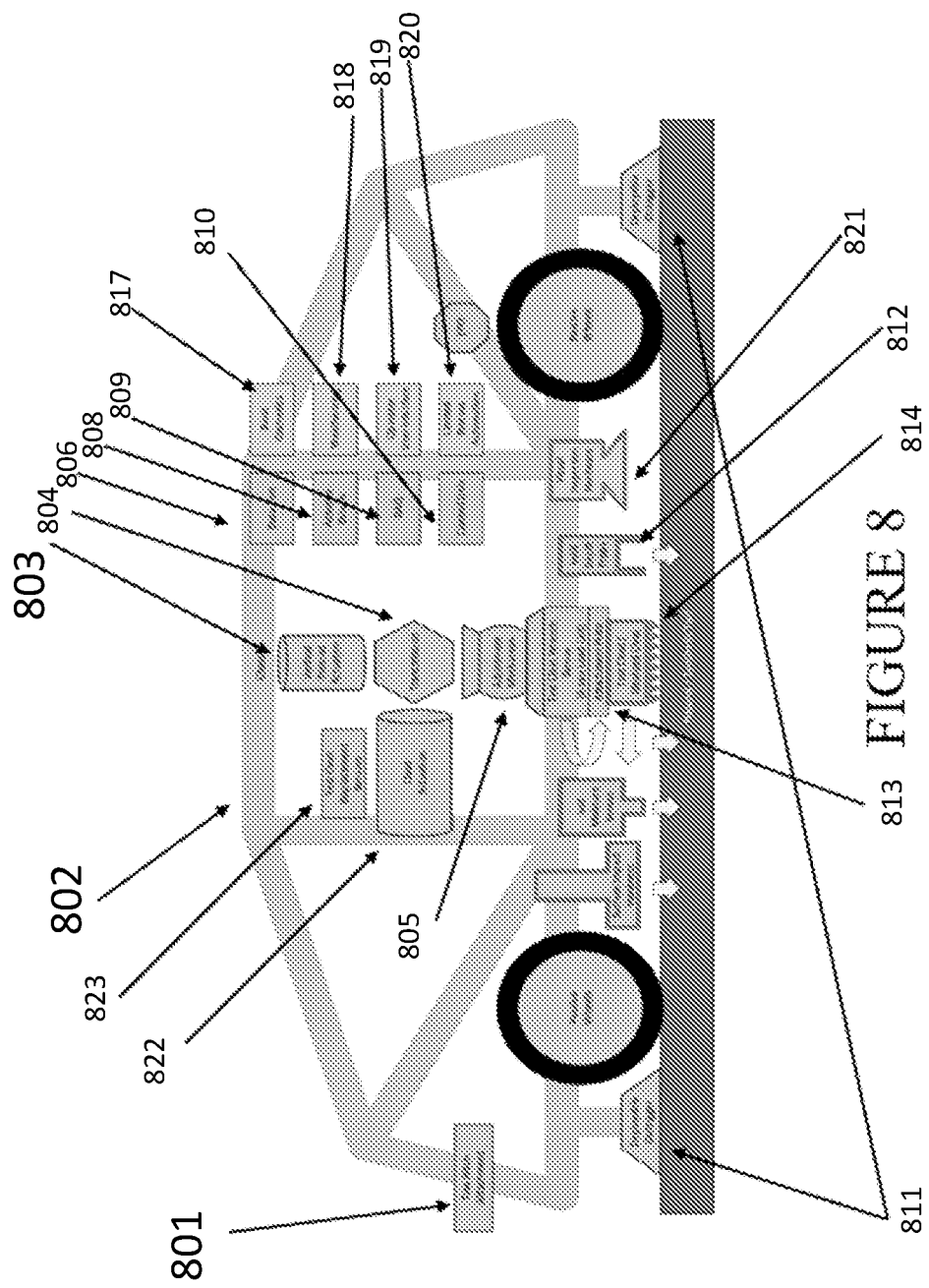
FIG. 8 is a depiction of the apparatus for athletic apparel and turf testing, including labeled aspects comprising parts of the apparatus, according to one embodiment of the present invention.
Figure 9:
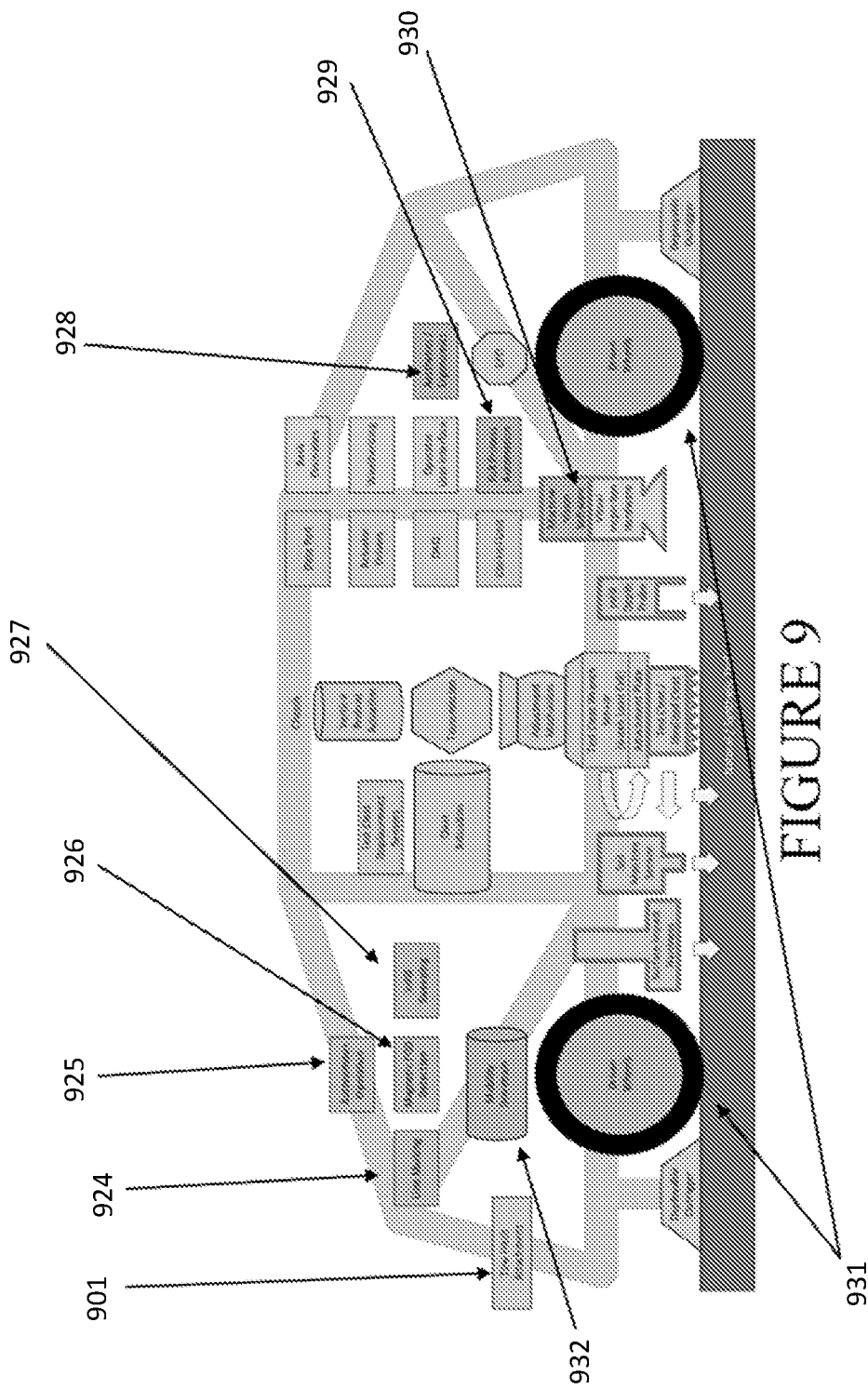
FIG. 9 is a depiction of the apparatus for athletic apparel and turf testing, including labeled aspects comprising parts of the apparatus, according to one embodiment of the present invention.

For system architectural embodiments, shown in FIGS. 7-9, the apparatus may comprise additional elements, including but not limited to the capability to mark lines on the turf 924 (such as hash marks), user interface aesthetics and ergonomics 928, full process automation 929, a mechanism for autonomous operation 925, magnetic foreign object debris (FOD) detection 926, and the capability to infill sweep 927. In the embodiment shown in FIG. 9, for example, the apparatus is shown wherein it can be driven, including driven wheels 931 and a mobility drivetrain 932. This embodiment also shows where the camera or other visual inspection mechanism use machine vision technology/hardware and software 930.

In further aspects of the invention, the apparatus can be configured to include some or all of the mentioned elements such as line marking, magnetic FOD detection, infill sweeping, testing infill for bacteria agents, automatic data uploading to server, automated all user processes, fully autonomous system, and/or drone assist full field inspection from above.

Figure 10:
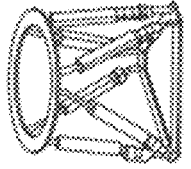
FIG. 10 is a depiction of various aspects of the apparatus for athletic apparel and turf testing, according to one embodiment of the present invention.

As shown in FIGS. 10 and 23, by way of example, the target power numbers may include up to a 8 kN preload, a horizontal (longitudinal or lateral or oblique) force range up to 10 kN, and a torque range up to 400 Nm. Displacement may include up to 500 mm translation and/or up to 225 degrees rotation. Instantaneous power requirements may be accomplished via a multi-actuator driven system. In other aspects, a hydraulic Stewart platform may be used. Due to the design of the current invention, it allows for higher forces to be applied, including up to providing 400 Newton-meters of torque; up to 8,000 Newtons of vertical force; and up to 10,000 Newtons of horizontal force; individually or at the same time. In a particular embodiment, by way of example, vertical preload may be from 0.10-6.0 kN, translation pull force may be up to 10 kN, rotational torque may be up to 400 Nm, translation speed may be around 3.5 m/s, rotation speed may be around 2500 deg/sec [43.6 rad/s], and cleat-turf interface adjustability is possible in the roll, pitch, and yaw orientations/directions. The invention may also limit compliance of the footform in unconstrained degrees of freedom during the shoe-surface interaction, so that test conditions are maintained as accurately as possible. The invention is intended to operate in temperatures ranging from, but not limited to, 0-100 degrees Fahrenheit. In one embodiment of the invention, the size of the invention may be approximately 7.0 feet long by 4.0 feet wide by 4.0 feet high, while the weight may be between 1,000-3,000 lbs.

Figure 2:
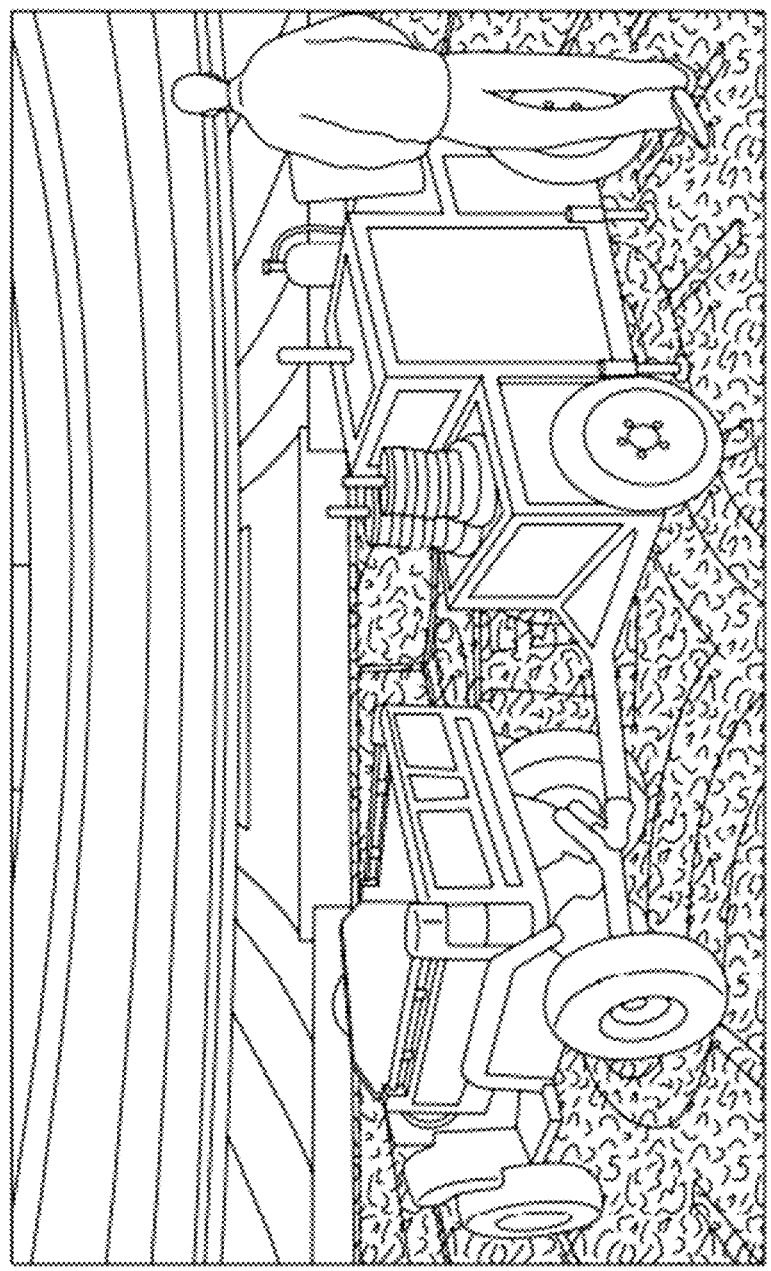
FIG. 2 is a depiction of the apparatus for athletic apparel and turf testing, according to one embodiment of the present invention.
Figure 11:
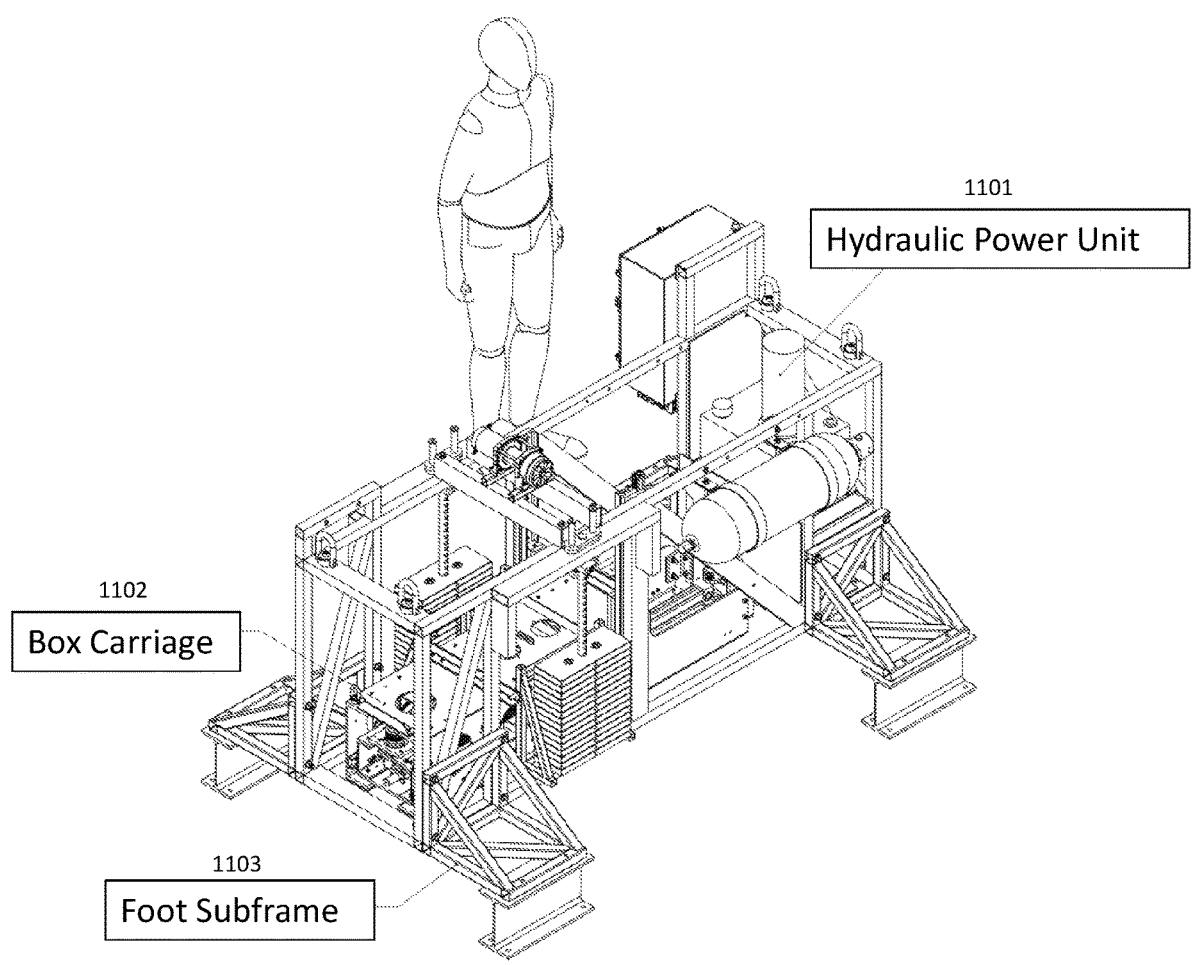
FIG. 11 is a depiction of the apparatus for athletic apparel and turf testing, including labeled aspects comprising parts of the apparatus, according to one embodiment of the present invention.
Figure 12:
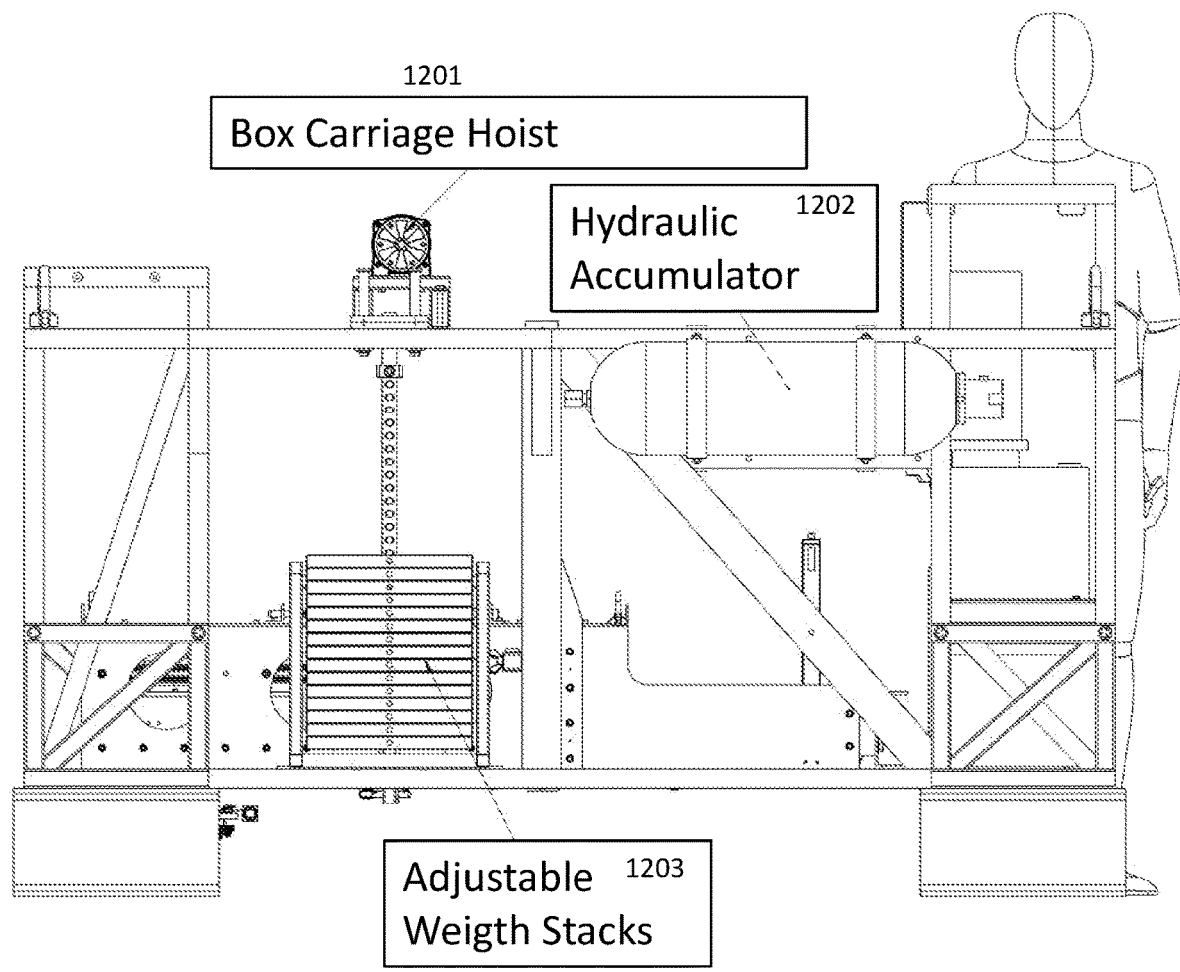
FIG. 12 is a depiction of the apparatus for athletic apparel and turf testing, including labeled aspects comprising parts of the apparatus, according to one embodiment of the present invention.
Figure 13:
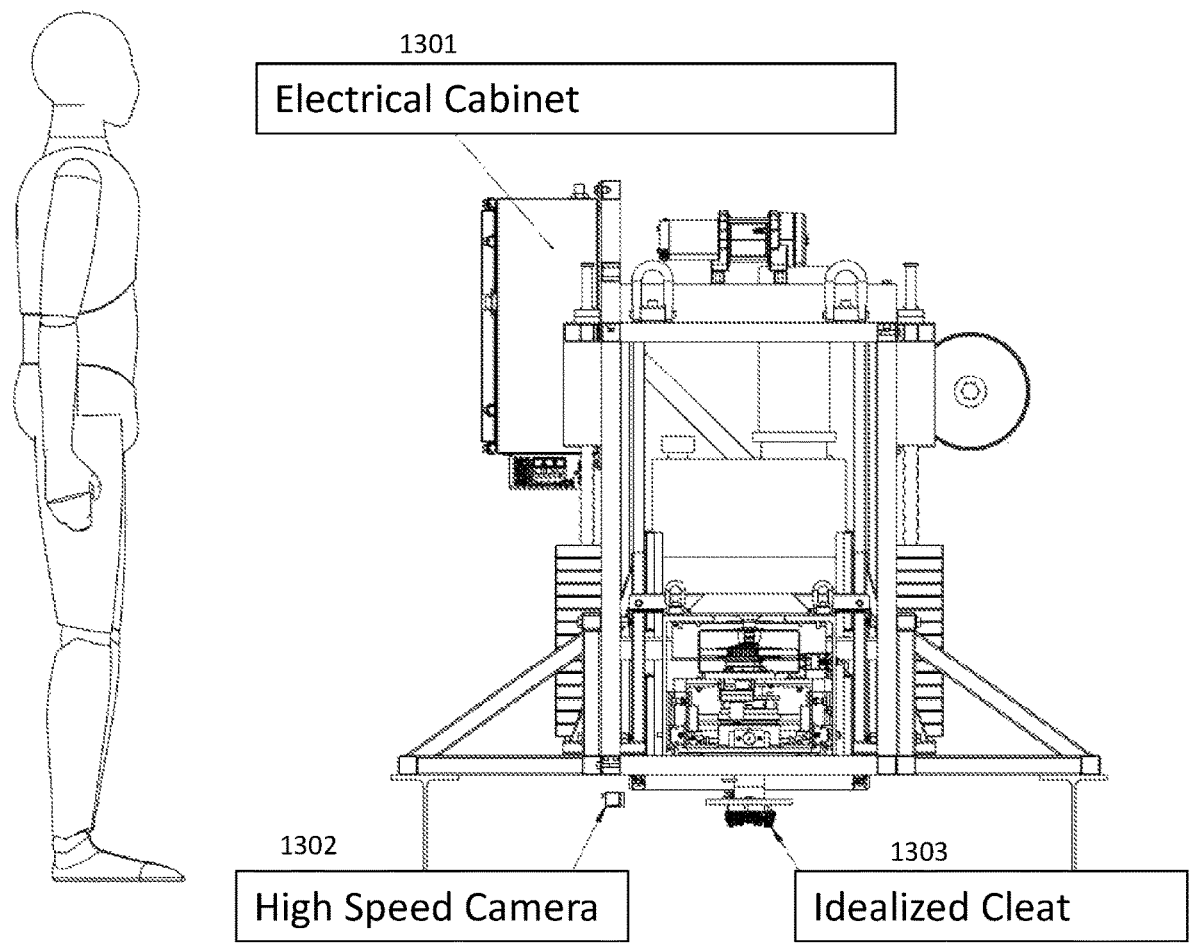
FIG. 13 is a depiction of the apparatus for athletic apparel and turf testing, including labeled aspects comprising parts of the apparatus, according to one embodiment of the present invention.
Figure 14:
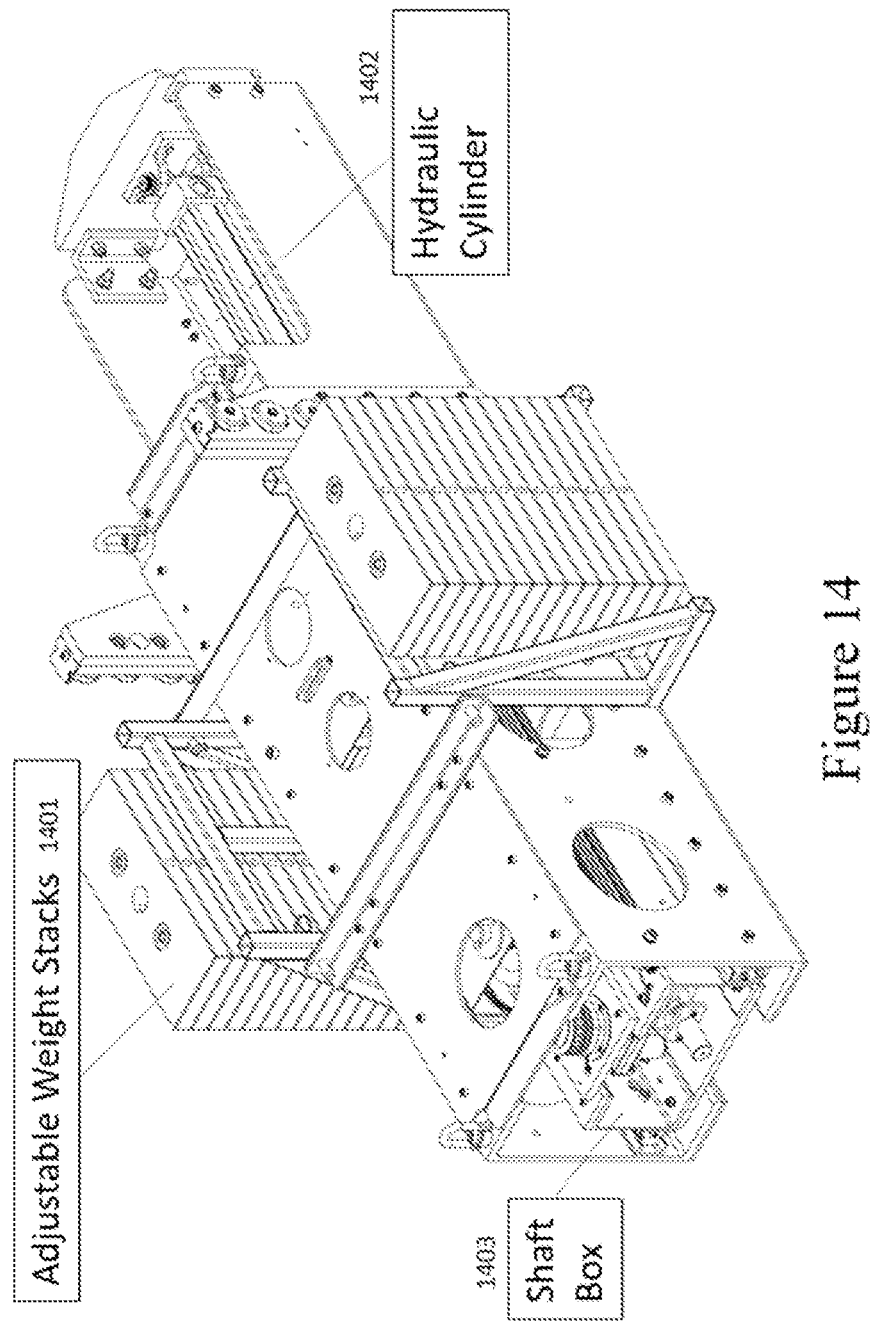
FIG. 14 is a depiction of the apparatus for athletic apparel and turf testing, including labeled aspects comprising parts of the apparatus, according to one embodiment of the present invention.
Figure 15:
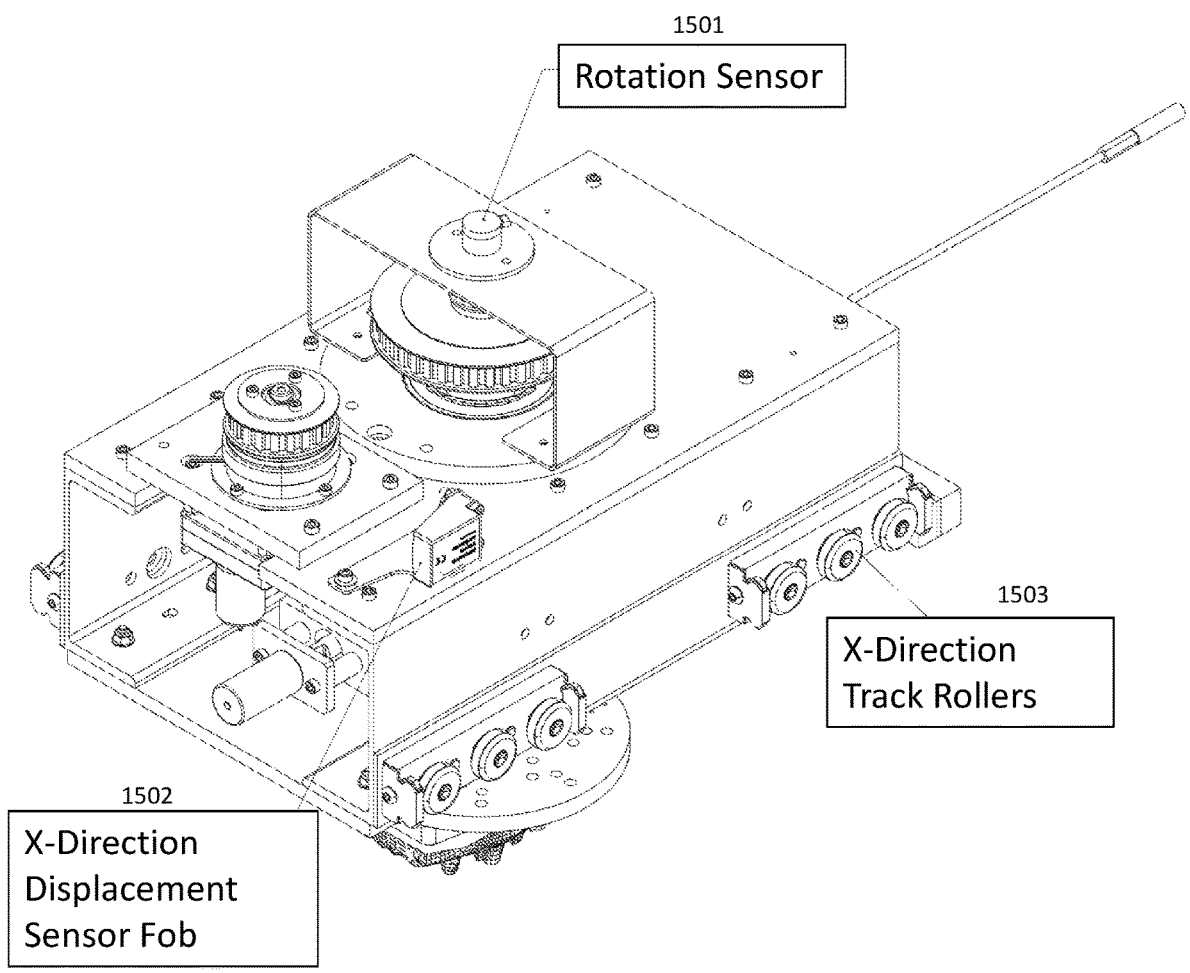
FIG. 15 is a depiction of the apparatus for athletic apparel and turf testing, including labeled aspects comprising parts of the apparatus, according to one embodiment of the present invention.
Figure 16:
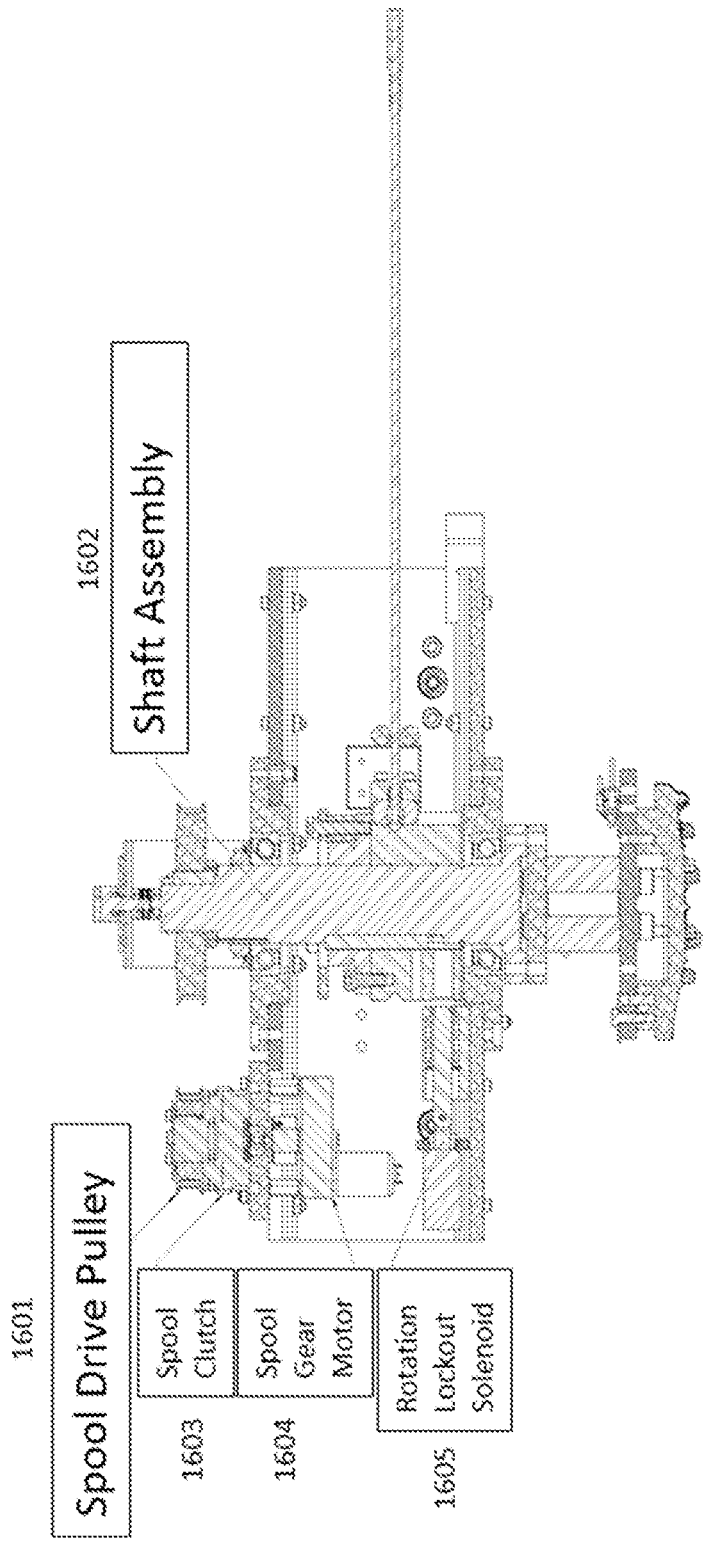
FIG. 16 is a depiction of the apparatus for athletic apparel and turf testing, including labeled aspects comprising parts of the apparatus, according to one embodiment of the present invention.
Figure 17:
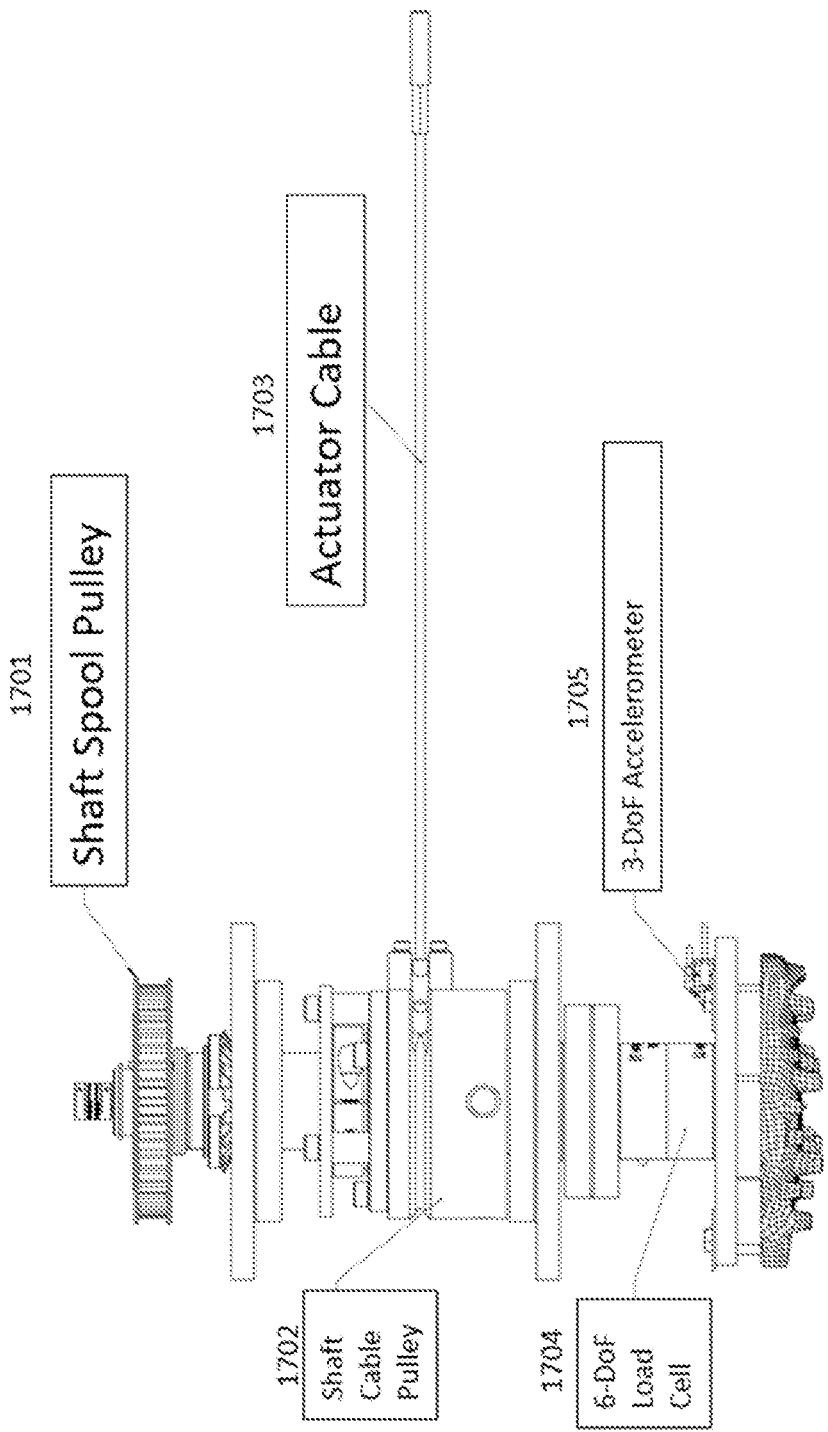
FIG. 17 is a depiction of the apparatus for athletic apparel and turf testing, including labeled aspects comprising parts of the apparatus, according to one embodiment of the present invention.
Figure 18:
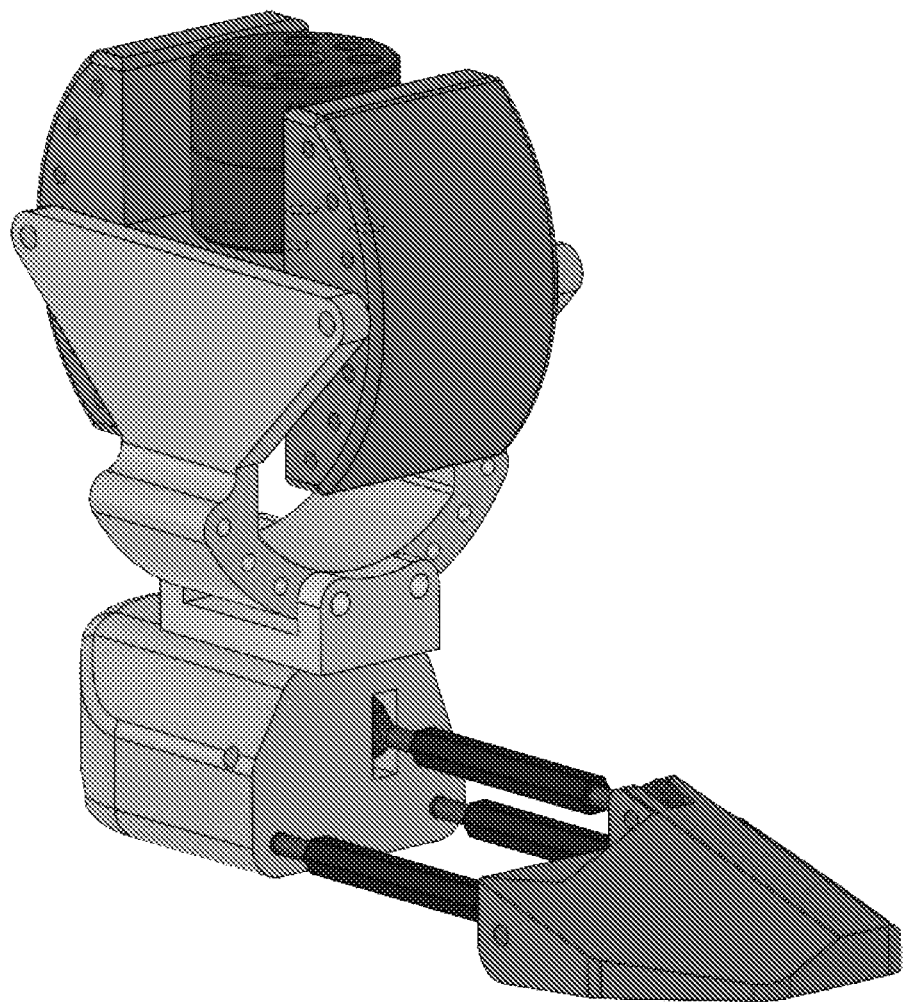
FIG. 18 is a depiction of an aspects of the apparatus for athletic apparel and turf testing, according to one embodiment of the present invention.
Figure 20A:
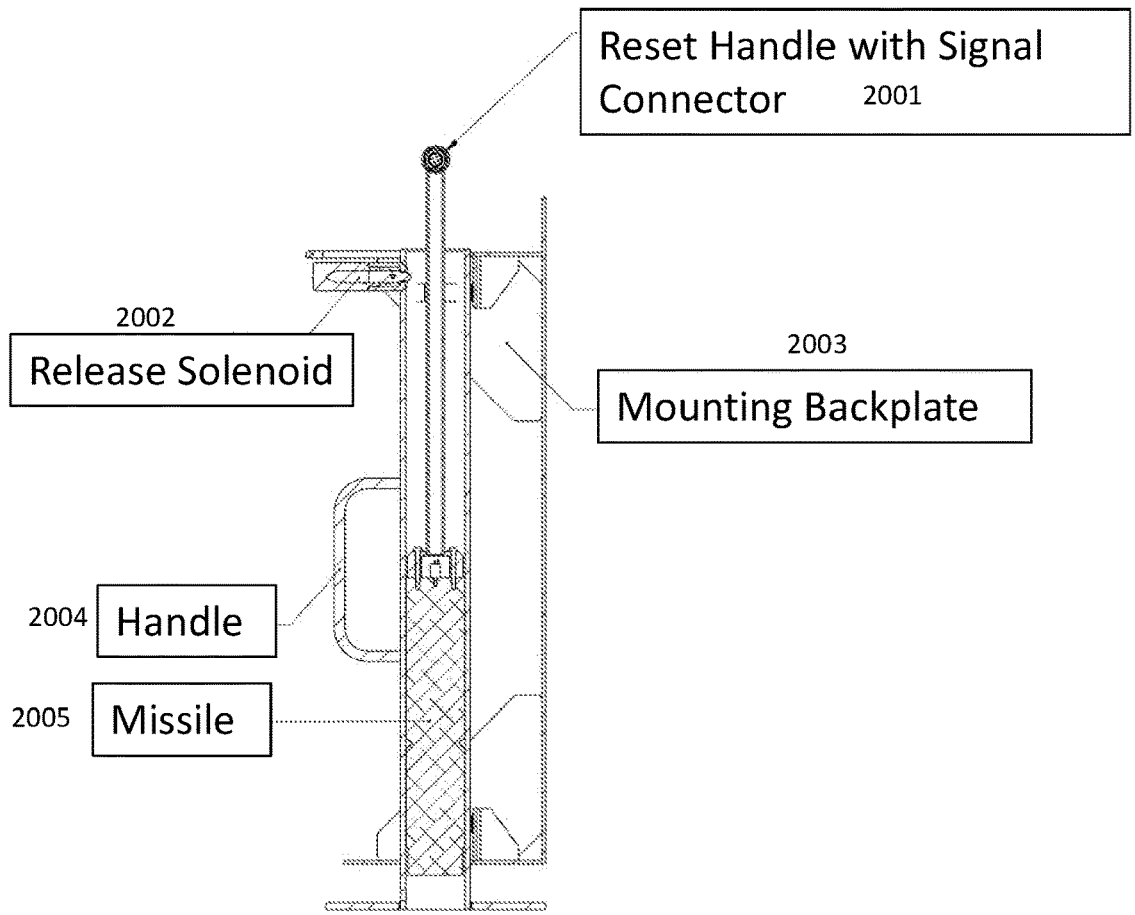
FIG. 20A is a depiction of the apparatus for athletic apparel and turf testing, including labeled aspects comprising parts of the apparatus, according to one embodiment of the present invention.
Figure 20B:
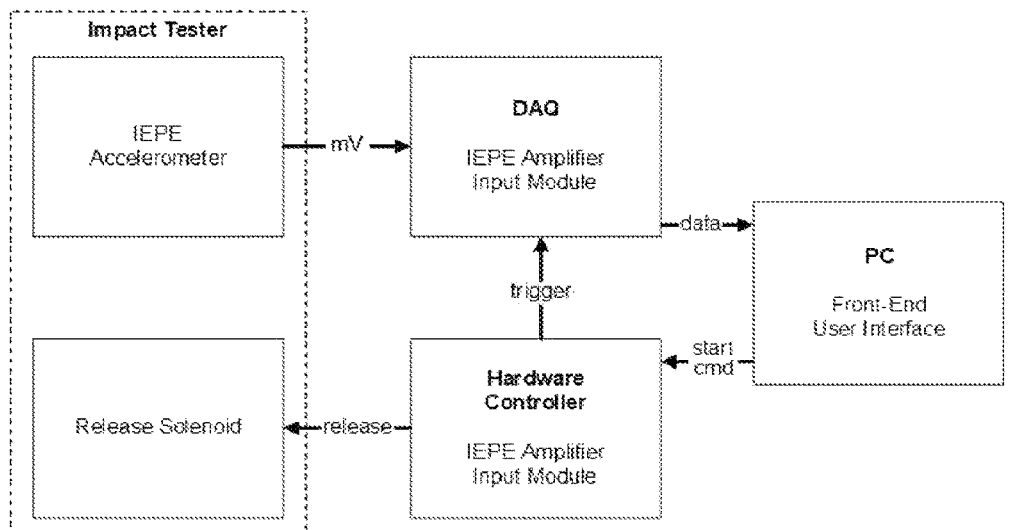
FIG. 20B is a diagram of an integration data collection logic loop according to an embodiment of the present invention.
Figure 21:
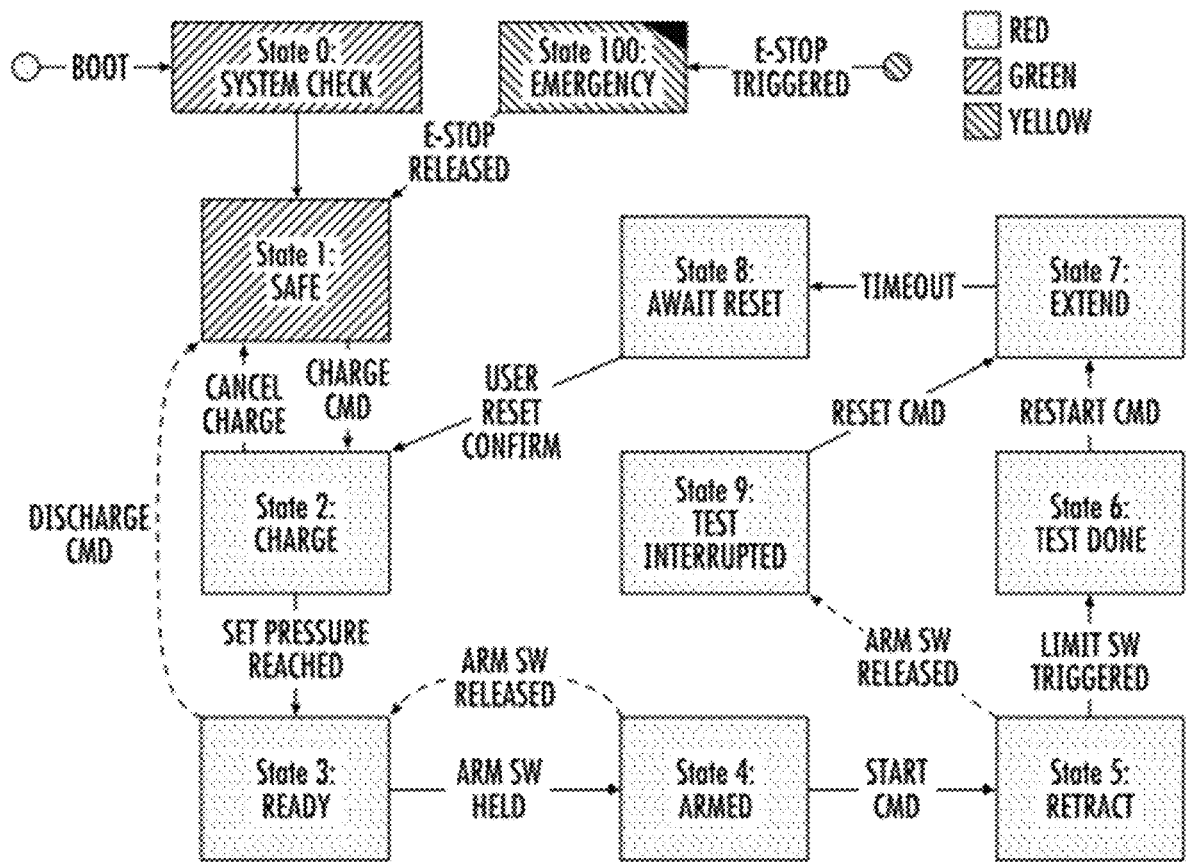
FIG. 21 is a depiction of the actuation architecture according to one embodiment of the present invention.

Design schematics comprise several other Figures. FIG. 1 shows an embodiment of the invention including aesthetic paneling and molded material covering the internal structure of the apparatus. In this particular embodiment, the apparatus may be driven manually or autonomously, or by remote control. In FIG. 2 and FIG. 3, an embodiment is shown of the apparatus wherein it is passive and towed by another vehicle, with and without exterior body panels. Similarly, in FIGS. 5 and 6, the apparatus is shown with add-ons that extend capability by increasing stability and with touch-screen human-machine interface, respectively. FIGS. 7-9 show embodiments of system architecture of the core device (see, e.g., FIG. 7), as well as with add-on systems that extend capability, such as computer vision (see, e.g., FIG. 8), and self-propulsion (see, e.g., FIG. 9). FIG. 10 is an example of hardware available for test actuation in the load and rate regimes to replicate athlete cleat-turf interactions. FIGS. 11-13 show embodiments of design schematics for the full device in isometric, side, and front reliefs, respectively. A notional human is provided for scale. Specifically, FIG. 11 shows the apparatus including a box carriage 1102, hydraulic power unit 1101, and foot subframe 1103. FIG. 12 shows the apparatus including a box carriage hoist 1201, a hydraulic accumulator 1202, and an adjustable weight stack 1203. FIG. 13 shows the apparatus including an electrical cabinet 1301, a high-speed camera 1302, and an idealized cleat 1303. FIGS. 14-17 show design schematics for embodiments of the mechanical subsystems governing the mechanism translation (see FIG. 14) and rotation (see FIGS. 15-17). Specifically, FIG. 14 shows a subsystem including adjustable weight stacks 1401, hydraulic cylinder 1402, and a shaft box 1403. FIG. 15 shows a subsystem including a rotation sensor 1501, an x-direction displacement sensor fob 1502, and x-direction track rollers 1503. FIG. 16 shows a subsystem including a spool drive pulley 1601, a shaft assembly 1602, a spool clutch 1603, a spool gear motor 1604, and a rotation lockout solenoid 1605. FIG. 17 shows a subsystem including a shaft spool pulley 1701, a shaft cable pulley 1702, an actuator cable 1703, a 6-DoF load cell 1704, and a 3-DoF accelerometer 1705. FIG. 18 is a design schematic of an embodiment of the surrogate footform, capable of articulating at the 'ankle' and 'toe' joints, in this example, whilst being shod in standard footwear. FIG. 19 is a design schematic of an embodiment of the turf datum finder for establishing a reference height of the turf relative to the rest of the device actuation assembly, including a non-contact limit switch 1901, a cage with mounting flange 1902, and a probe stem 1903. FIG. 20A shows a design schematic of an embodiment of the impact test device, including a reset handle with signal connection 2001, a release solenoid 2002, a mounting backplate 2003, a handle 2004, and a missle 2005, and FIG. 20B shows its integration data collection logic loop. FIG. 21 is a diagram outlining an embodiment of the actuator and power states of the device during different set points in the acquisition process. FIG. 22 shows and automatic control logic diagram for an embodiment of the device, allowing for the use of real-time or near-real-time computer-mediated adjustments to the device actuation in response to the loads/moments perceived at the cleat-turf interface. FIG. 23 is a power flow diagram outlining an embodiment of how the electrical and pneumatic power systems communicate across the device to actuate the device mechanism.

Figure 6:
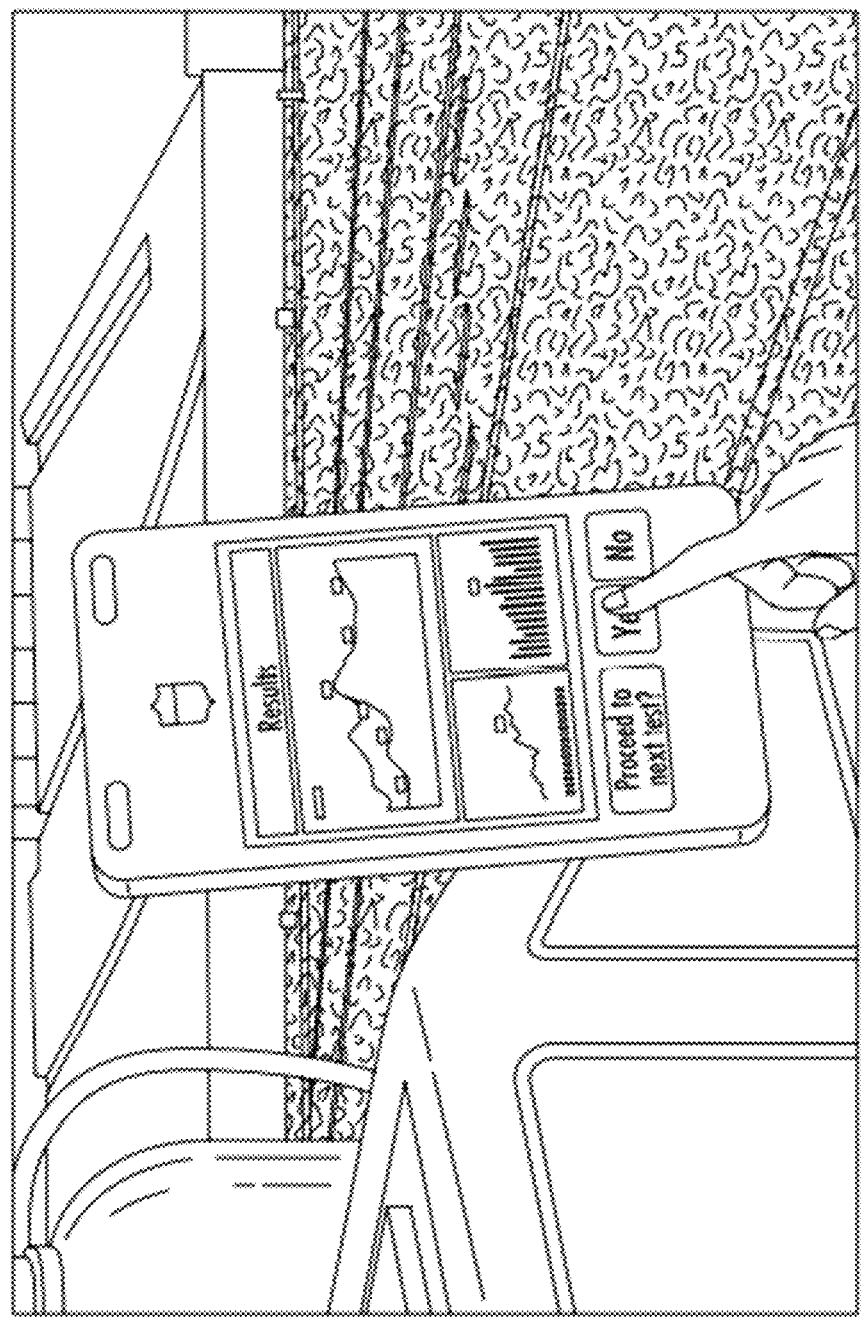
FIG. 6 is a depiction showing using the apparatus via a touchscreen computer module (e.g., a tablet computer or mobile phone), according to one embodiment of the present invention.

FIG. 6 shows that a tablet computer, mobile phone, or other portable electronic device may be used to control the apparatus and/or review the test data, by way of example only. Embodiments of the invention include a computer readable medium comprising one or more computer files comprising a set of computer-executable instructions for performing one or more of the calculations, steps, processes and operations described and/or depicted herein. In exemplary embodiments, the files may be stored contiguously or non-contiguously on the computer-readable medium. In aspects, the files or data may be sent directly or indirectly to the cloud or remote servers(s). Embodiments may include a computer program product comprising the computer files, either in the form of the computer-readable medium comprising the computer files and, optionally, made available to a consumer through packaging, or alternatively made available to a consumer through electronic distribution. As used in the context of this specification, a "computer-readable medium" is a non-transitory computer-readable medium and includes any kind of computer memory such as floppy disks, conventional hard disks, CD-ROM, Flash ROM, non-volatile ROM, electrically erasable programmable read-only memory (EEPROM), and RAM. In exemplary embodiments, the computer readable medium has a set of instructions stored thereon which, when executed by a processor, cause the processor to perform tasks, based on data stored in the electronic database or memory described herein. The processor may implement this process through any of the procedures discussed in this disclosure or through any equivalent procedure.

In other embodiments of the invention, files comprising the set of computer-executable instructions may be stored in computer-readable memory on a single computer or distributed across multiple computers or involve a network of remote servers hosted on the internet. In aspects, local, edge, or remote computing possibilities are used to store, manage, and process data. A skilled artisan will further appreciate, in light of this disclosure, how the invention can be implemented, in addition to software, using hardware or firmware. As such, as used herein, the operations of the invention can be implemented in a system comprising a combination of software, hardware, or firmware.

Embodiments of this disclosure include one or more computers or devices loaded with a set of the computer-executable instructions described herein. The computers or devices may be a general-purpose computer, a special-purpose computer, or other programmable data processing apparatus to produce a particular machine, such that the one or more computers or devices are instructed and configured to carry out the calculations, processes, steps, operations, algorithms, statistical methods, formulas, or computational routines of this disclosure. The computer or device performing the specified calculations, processes, steps, operations, algorithms, statistical methods, formulas, or computational routines of this disclosure may comprise at least one processing element such as a central processing unit (i.e., processor) and a form of computer-readable memory which may include random-access memory (RAM) or read-only memory (ROM). The computer-executable instructions can be embedded in computer hardware or stored in the computer-readable memory such that the computer or device may be directed to perform one or more of the calculations, steps, processes, and operations depicted and/or described herein.

Additional embodiments of this disclosure comprise a computer system for carrying out the computer-implemented method of this disclosure. The computer system may comprise a processor for executing the computer-executable instructions, one or more electronic databases containing the data or information described herein, an input/output interface or user interface, and a set of instructions (e.g., software) for carrying out the method. The computer system can include a stand-alone computer, such as a desktop computer, a portable computer, such as a tablet, laptop, PDA, or smartphone, or a set of computers connected through a network including a client-server configuration and one or more database servers. The network may use any suitable network protocol, including IP, UDP, or ICMP, and may be any suitable wired or wireless network including any local area network, wide area network, Internet network, telecommunications network, Wi-Fi enabled network, or Bluetooth enabled network. In one embodiment, the computer system comprises a central computer connected to the internet that has the computer-executable instructions stored in memory that is operably connected to an internal electronic database. The central computer may perform the computer-implemented method based on input and commands received from remote computers through the internet. The central computer may effectively serve as a server and the remote computers may serve as client computers such that the server-client relationship is established, and the client computers issue queries or receive output from the server over a network.

The input/output interfaces may include a graphical user interface (GUI) which may be used in conjunction with the computer-executable code and electronic databases. The graphical user interface may allow a user to perform these tasks through the use of text fields, check boxes, pull-downs, command buttons, and the like. A skilled artisan will appreciate how such graphical features may be implemented for performing the tasks of this disclosure. The user interface may optionally be accessible through a computer connected to the internet. In one embodiment, the user interface is accessible by typing in an internet address through an industry standard web browser and logging into a web page. The user interface may then be operated through a remote computer (client computer) accessing the web page and transmitting queries or receiving output from a server through a network connection.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A portable apparatus comprising:
    a chassis or frame;
    one or more processors;
    a hydraulic power unit and/or weights; and
    a translation-rotation footform having roll, pitch, and yaw adjustability;
    wherein the footform is capable of being shod with footwear;
    wherein the footform shod with footwear engages with a surface to apply horizontal, vertical, and rotational forces to the footform shod with footwear;
    wherein the applied forces are maintained at a set level or rate; and
    wherein applying and measuring interactions between the applied forces at the same or different times allows for the capability to evaluate safety and/or performance of the footwear or the surface.

2. The portable apparatus of claim 1, further comprising a user interface capable of generating or presenting data, data analysis, or data interpretation.

3. The portable apparatus of claim 1, wherein the one or more processors are located remotely from the portable apparatus.

4. The portable apparatus of claim 1, wherein the one or more processors communicates with a remote electronic device.

5. The portable apparatus of claim 1, wherein the footform comprises one or more sensors.

6. The portable apparatus of claim 1, wherein the apparatus collects data from the footform engaging with the surface, and wherein the apparatus, a user of the apparatus, the one or more processors, or a computer analyzing data from the apparatus measures or evaluates the footwear release dynamics based on data from the footform engaging with the surface.

7. The portable apparatus of claim 1, wherein the footform adjustability allows the apparatus to collect data on footwear-to-surface interface angles.

8. The portable apparatus of claim 1, wherein the footform adjustability allows for adjustment to an angle of a first portion of the footform relative to a second portion of the footform.

9. The portable apparatus of claim 1, wherein the adjustability allows the apparatus to approximate flexion of a human foot about a human metatarsophalangeal joint.

10. The portable apparatus of claim 1, wherein the apparatus or footform is capable of maintaining or holding adjustments to roll, pitch, and yaw fixed or in a static pose while using the apparatus.

11. The portable apparatus of claim 1, further comprising an end effector attached to a translation and rotation actuation mechanism via a multi-axis load cell.

12. The portable apparatus of claim 1, further comprising one or more rotational sensors and one or more translational displacement sensors, wherein the one or more processors is capable of recording data from the one or more rotational sensors and one or more translational displacement sensors.

13. The portable apparatus of claim 12, wherein the one or more processors in conjunction with the one or more rotational sensors or one or more translational displacement sensors is capable of detecting a linear position and velocity of the footwear.

14. The portable apparatus of claim 13, further comprising a footform capable of being shod with footwear, wherein the processor in conjunction with the rotational sensor or translational displacement sensor is capable of detecting angular rotations and velocities of the footwear.

15. The portable apparatus of claim 1, wherein accelerations of the footform are measured to characterize an interaction of the footwear with the surface, or wherein accelerations of the footform are measured to characterize inertial effects of the apparatus during use.

16. The portable apparatus of claim 1, further comprising one or more cameras providing computer-aided visual inspection of the surface.

17. The portable apparatus of claim 16, wherein the visual inspection uses machine learning visual recognition technologies and/or data synchronization.

18. The portable apparatus of claim 1, further comprising one or more cameras providing computer-aided visual inspection of the surface before, during, or after the apparatus applies and measures the interactions between the set forces.

19. The portable apparatus of claim 1, further comprising one or more sensors capable of measuring energy absorption and rebound/return through measurement of acceleration of a mass or mass-spring system dropped onto the surface.

20. The portable apparatus of claim 1, further comprising one or more sensors capable of measuring surface hardness.

21. The portable apparatus of claim 1, further comprising one or more depth measurement mechanisms or sensors.

22. The portable apparatus of claim 1, further comprising one or more sensors capable of assessing surface stability using surface shear resistance and/or a connected shear vane.

23. The portable apparatus of claim 1, further comprising one or more sensors capable of detecting surface moisture levels.

24. The portable apparatus of claim 1, further comprising one or more sensors capable of measuring environmental factors including one or more of air temperature, ground temperature, surface temperature, air humidity, or combinations thereof.

25. The portable apparatus of claim 1, further comprising one or more sensors capable of measuring or evaluating a top surface of natural or artificial turf.

26. The portable apparatus of claim 1, wherein the one or more processors are capable of providing scoring or rankings of the footwear or the surface.

27. The portable apparatus of claim 1, wherein the portable apparatus is capable of providing one or more of the following capabilities:
   (a) compile test results and display them through a user interface;
   (b) compare test results against hard-coded or server-based scientifically-determined baseline data to score test results against;
   (c) compile and analyze force/torque test results with other test result streams and display to a user;
   (d) retrieve historical results from tests and compare with baseline hard-coded data or compare the retrieved historical results with new test data;
   (e) evaluate and score geographical consistency of a surface by registering more than one test with location using Global Positioning System and analyzing test results from multiple locations using correlation, coefficient of variation, standard error, standard deviation, or combinations thereof to assess variability;
   (f) score or rank footwear by analyzing a mechanical response of different footwear;
   (g) flag or recommend localized intervention if a surface may be dangerous;
   (h) collect, register, synchronize, retrieve, and/or analyze metadata related to the footwear or the surface; and/or
   (i) display video of a test against a force/displacement or displacement/time result.

28. A portable apparatus comprising:
a chassis or frame;
one or more processors;
one or more sensors;
a hydraulic power unit and/or weights; and
a translation-rotation footform having roll, pitch, and yaw adjustability;
wherein the footform is capable of being shod with footwear;
wherein the footform shod with footwear engages with a surface to apply horizontal, vertical, and rotational forces to the footform shod with footwear;
wherein the apparatus or footform is capable of maintaining or holding adjustments to roll, pitch, and yaw fixed or in a static pose when the apparatus is in use.

* * * * *